US008747368B2

(12) United States Patent
Mernoe et al.

(10) Patent No.: US 8,747,368 B2
(45) Date of Patent: Jun. 10, 2014

(54) DISPENSING FLUID FROM AN INFUSION PUMP SYSTEM

(75) Inventors: Morten Mernoe, Charlottenlund (DK); Mitchell Wenger, Ross, CA (US); James Causey, Simi Valley, CA (US); Todd Kirschen, Palo Alto, CA (US)

(73) Assignee: Asante Solutions, Inc., Sunnyvale, CA (US)

( * ) Notice: Subject to any disclaimer, the term of this patent is extended or adjusted under 35 U.S.C. 154(b) by 6 days.

(21) Appl. No.: 13/358,330

(22) Filed: Jan. 25, 2012

(65) Prior Publication Data
US 2012/0123384 A1 May 17, 2012

Related U.S. Application Data

(62) Division of application No. 11/522,836, filed on Sep. 18, 2006, now Pat. No. 8,105,279.

(60) Provisional application No. 60/720,405, filed on Sep. 26, 2005, provisional application No. 60/720,411, filed on Sep. 26, 2005, provisional application No. 60/721,267, filed on Sep. 28, 2005.

(51) Int. Cl.
*A61M 5/00* (2006.01)
*A61M 1/00* (2006.01)

(52) U.S. Cl.
USPC ............ 604/211; 604/151; 604/152; 604/207

(58) Field of Classification Search
USPC ........... 604/67, 152, 500, 207–211, 151, 131, 604/890.1
See application file for complete search history.

(56) References Cited

U.S. PATENT DOCUMENTS

| 2,605,765 | A | 8/1952 | Kollsman |
| 3,886,938 | A | 6/1975 | Szabo et al. |
| 4,077,405 | A | 3/1978 | Haerten et al. |
| 4,231,368 | A | 11/1980 | Becker |
| 4,265,241 | A | 5/1981 | Portner et al. |
| 4,300,554 | A | 11/1981 | Hessberg et al. |
| 4,313,439 | A | 2/1982 | Babb et al. |
| 4,373,527 | A | 2/1983 | Fischell |

(Continued)

FOREIGN PATENT DOCUMENTS

| CA | 2543545 | 5/2005 |
| DE | 196 27 619 | 1/1998 |

(Continued)

OTHER PUBLICATIONS

Accu-Chek Spirit, "Pump Therapy Made for You," Roche, 2006, 6 pages.

(Continued)

*Primary Examiner* — Bhisma Mehta
*Assistant Examiner* — Bradley G Thomas, Jr.
(74) *Attorney, Agent, or Firm* — Fish & Richardson P.C.

(57) ABSTRACT

Some embodiments of a medical infusion pump system include a pump device having a flexible pushrod that can adjust from a curved configuration to a generally straight configuration. The flexible pushrod is part of a drive system of the pump device so that the flexible pushrod can be controllably and incrementally advanced toward a medicine reservoir to incrementally dispense the medicine therein. In particular embodiments, the flexible pushrod may comprise an anti-rotation mechanism, an anti-torsion mechanism, or a combination thereof.

20 Claims, 14 Drawing Sheets

(56) References Cited

U.S. PATENT DOCUMENTS

| | | |
|---|---|---|
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,619,653 A | 10/1986 | Fischell |
| 4,850,817 A | 7/1989 | Nason et al. |
| 4,908,017 A * | 3/1990 | Howson et al. .......... 604/67 |
| 4,980,017 A | 12/1990 | Kaji et al. |
| 4,990,133 A | 2/1991 | Solazzo |
| 5,045,064 A | 9/1991 | Idriss |
| 5,088,981 A | 2/1992 | Howson et al. |
| 5,190,522 A | 3/1993 | Wojcicki et al. |
| 5,250,027 A | 10/1993 | Lewis et al. |
| 5,261,882 A | 11/1993 | Sealfon et al. |
| 5,314,412 A | 5/1994 | Rex |
| 5,335,994 A | 8/1994 | Weynant nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell |
| 5,551,850 A | 9/1996 | Williamson et al. |
| 5,569,186 A | 10/1996 | Lord et al. |
| 5,626,566 A | 5/1997 | Petersen et al. |
| 5,637,095 A | 6/1997 | Nason et al. |
| 5,665,065 A | 9/1997 | Colman et al. |
| 5,741,216 A | 4/1998 | Hemmingsen et al. |
| 5,764,034 A | 6/1998 | Bowman et al. |
| 5,772,635 A | 6/1998 | Dastur et al. |
| 5,816,306 A | 10/1998 | Giacomel |
| 5,852,803 A | 12/1998 | Ashby, III et al. |
| 5,919,167 A | 7/1999 | Mulhauser |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |

(56) References Cited

U.S. PATENT DOCUMENTS

| | | |
|---|---|---|
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,172,572 B2 | 2/2007 | Diamond et al. |
| 7,232,423 B2 | 6/2007 | Mernoe et al. |
| 2001/0041869 A1 | 11/2001 | Causey, III et al. |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0016568 A1 | 2/2002 | Lebel |
| 2002/0032402 A1 | 3/2002 | Daoud et al. |
| 2002/0040208 A1 | 4/2002 | Flaherty et al. |
| 2002/0091358 A1* | 7/2002 | Klitmose .............. 604/131 |
| 2002/0126036 A1 | 9/2002 | Flaherty et al. |
| 2002/0156462 A1 | 10/2002 | Stultz |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0161744 A1 | 8/2003 | Vilks et al. |
| 2003/0198558 A1 | 10/2003 | Nason et al. |
| 2003/0199825 A1 | 10/2003 | Flaherty |
| 2003/0216683 A1 | 11/2003 | Shekalim |
| 2003/0216686 A1 | 11/2003 | Lynch et al. |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0115068 A1 | 6/2004 | Hansen et al. |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0187952 A1 | 9/2004 | Jones |
| 2004/0204673 A1 | 10/2004 | Flaherty |
| 2004/0204744 A1 | 10/2004 | Penner et al. |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0113745 A1 | 5/2005 | Stultz |
| 2005/0124866 A1 | 6/2005 | Elaz et al. |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073236 A1 | 3/2007 | Mernoe et al. |
| 2007/0088271 A1 | 4/2007 | Richards |
| 2007/0106218 A1 | 5/2007 | Yodfat et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0203459 A1 | 8/2007 | Mernoe |

FOREIGN PATENT DOCUMENTS

| | | |
|---|---|---|
| DE | 102 36 669 | 2/2004 |
| DK | PA 2004/01893 | 12/2004 |
| EP | 0 062 974 | 10/1982 |
| EP | 0 496 141 | 7/1992 |
| EP | 0 612 004 | 8/1994 |
| EP | 0 580 723 | 10/1995 |
| EP | 0 275 213 | 7/1998 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| EP | 1754498 | 2/2007 |
| EP | 1 818 664 | 8/2007 |
| EP | 1818664 | 8/2007 |
| FR | 2 585 252 | 1/1987 |
| GB | 747 701 | 4/1956 |
| GB | 2 218 831 | 11/1989 |
| GB | 2218831 | 11/1989 |
| JP | A 9-504974 | 5/1997 |
| JP | 2000-513974 | 10/2000 |
| JP | 2002-507459 | 3/2002 |
| JP | A 2002-523149 | 7/2002 |
| WO | WO 90/15928 | 12/1990 |
| WO | WO 97/21457 | 6/1997 |
| WO | WO 98/04301 | 2/1998 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/54753 | 8/2001 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/05/7627 | 7/2002 |
| WO | WO 02/068015 | 9/2002 |
| WO | WO 02/084336 | 10/2002 |
| WO | WO 02/100469 | 12/2002 |
| WO | WO 03/026726 | 4/2003 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2005072795 * | 8/2005 |
| WO | WO 2006/067217 | 6/2006 |
| WO | WO 2006/097453 | 9/2006 |
| WO | WO 2006/105792 | 10/2006 |
| WO | WO 2006/105793 | 10/2006 |
| WO | WO 2006/105794 | 10/2006 |
| WO | WO 2007/141786 | 12/2007 |

OTHER PUBLICATIONS

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

(56) References Cited

OTHER PUBLICATIONS

Medtronic News Release, "Medtronic Receives FDA Approval for World's First Insulin Pump with Real-time Continuous Glucose Monitoring," Apr. 13, 2006, 3 pages.
OmniPod Insulin Management System—Investor Relations—Press Release, Feb. 1, 2005, http://investors.insulet.com/phoenix.zhtml?c=209336&p=irol-newsArticle&ID=988708&highlight= 1 page.
OmniPod Quick Start Guide, 2007, 2 pages.
Patent Abstracts of Japan, vol. 1999, No. 04, and JP 11 010036, Apr. 30, 1999 and Jan. 19, 1999, Toray Ind. Inc.
The Medtronic Diabetes Connection, 2006, 6 pages.
Xilas Temp Touch, "The latest in high-tech and convenient devices," DOCNews, vol. 2, No. 7, Jul. 1, 2005, http://docnews.diabetesjournals.ord/cgi/content/full/2/7/13, 3 pages.

* cited by examiner

DISPENSING FLUID FROM AN INFUSION PUMP SYSTEM

CROSS-REFERENCE TO RELATED APPLICATIONS

This application is a division of U.S. application Ser. No. 11/522,836 filed on Sep. 18, 2006 by Mernoe et al., which claims priority to each of: (1) U.S. Provisional Application Ser. No. 60/720,411 filed on Sep. 26, 2005 by Mernoe et al. and entitled "Precision Drive Mechanism," (2) U.S. Provisional Application Ser. No. 60/720,405 filed on Sep. 26, 2005 by Mernoe et al. and entitled "Flexible Pushrod Mechanism," and (3) U.S. Provisional Application Ser. No. 60/721,267 filed on Sep. 28, 2005 by Estes et al. and entitled "Infusion Pump with Removable Controller." The contents of these previously filed applications are fully incorporated by reference herein.

TECHNICAL FIELD

This document relates to an infusion pump system, such as a medical infusion pump system.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

A number of factors may affect the design of infusion pump devices. One such factor is the size of the device. The pump device may be sized to house the various pump components, yet a large device may reduce the portability options and convenience for the user. A number of infusion pump components can impact the overall size and portability of an infusion pump system and the convenience to the user. For example, if a pump device includes a straight, rigid pushrod to force medicine from the infusion pump device, the pump housing is typically sized to accommodate the length of the rigid rod both when it is fully withdrawn from the reservoir and when it is fully extended into the reservoir.

SUMMARY

Some embodiments of a medical infusion pump system include a pump device having a pushrod that can adjust from a curved configuration to a generally straight configuration. The pushrod is part of a drive system of the pump device so that the pushrod can be controllably and incrementally advanced toward a medicine reservoir to incrementally dispense the medicine therein. In particular embodiments, the pushrod may comprise an anti-rotation mechanism, an anti-torsion mechanism, an anti-elongation mechanism, or a combination thereof.

In some embodiments, an infusion pump system for the delivery of medication may include a pump housing that defines a space to receive a medicine for dispensation and a drive system to dispense medicine when the medicine is received by the pump housing. The drive system may include a pushrod that is movable to apply a dispensing force to dispense medicine. The pushrod may include rod segments, and each rod segment may interconnected to the next rod segment by a hinge portion so that at least a portion of the pushrod is adjustable from a curved shape to a generally noncurved shape. The pushrod may also include an anti-rotation mechanism to oppose rotation of the pushrod about a longitudinal axis of the pushrod. The pushrod may further include an anti-torsion mechanism to oppose torsion of one rod segment relative to another rod segment.

Particular embodiments of an infusion pump system for the delivery of medication may include a pump housing that defines a space to receive a medicine for dispensation and a drive system to dispense medicine when the medicine is received by the pump housing. The drive system may include a pushrod that is movable to apply a dispensing force to dispense medicine. The pushrod may include rod segments that are hingedly engaged to one another such that at least a portion of the pushrod is adjustable from a curved shape to a generally noncurved shape. The pushrod may also include an anti-rotation mechanism to hinder rotation of the pushrod about a longitudinal axis of the pushrod. The anti-rotation mechanism may include two or more longitudinal channels extending through at least a plurality of the rod segments.

Some embodiments of an infusion pump system for the delivery of medication may include a pump housing that defines a space to receive a medicine for dispensation and a drive system to dispense medicine when the medicine is received by the pump housing. The drive system may include a pushrod that is movable to apply a dispensing force to dispense medicine. The pushrod may include rod segments that are hingedly engaged to one another such that at least a portion of the pushrod is adjustable from a curved shape to a generally noncurved shape. The pushrod may include an anti-torsion mechanism to oppose torsion of one rod segment relative to an adjacent rod segment. The anti-torsion mechanism may include an extended member protruding from the one rod segment that is engageable with a cavity disposed in the adjacent rod segment.

Certain embodiments of an infusion pump system for the delivery of medication may include a pump housing that defines a space to receive a medicine for dispensation and a drive system to dispense medicine when the medicine is received by the pump housing. The drive system may include a pushrod that is movable to apply a dispensing force to dispense medicine. The pushrod may include rod segments that are hingedly engaged to one another such that at least a portion of the pushrod is adjustable from a curved shape to a generally noncurved shape. The pushrod may include an anti-elongation mechanism disposed on at least a plurality of the pushrod segments to maintain the leading face of one pushrod segment in abutting relationship with a trailing face of an adjacent pushrod segment when a portion of the pushrod is adjusted to the generally noncurved shape.

In some embodiments, an infusion pump system for the delivery of medication may include a pump housing that defines a space to receive a medicine for dispensation and a drive system to dispense medicine when the medicine is received by the pump housing. The drive system may include a pushrod that is movable to apply a dispensing force to dispense medicine. The pushrod may include rod segments that are hingedly engaged to one another such that at least a portion of the pushrod is adjustable from a curved shape to a generally noncurved shape. Each of the hinge portions may comprise a flexible wire that extends from a leading face of one rod segment to a trailing face of an adjacent rod segment.

Some embodiments of an infusion pump system for the delivery of medication may include a pump housing that defines a space to receive a medicine for dispensation and a drive system to dispense medicine when the medicine is received by the pump housing. The drive system may include a pushrod that is movable to apply a dispensing force to dispense medicine. The pushrod may include mechanically assembled rod segments. Each rod segment may include a hinge protrusion that pivotably engages a hinge receiver cavity of the next rod segment in the row by a hinge assembly so that at least a portion of the pushrod is adjustable from a curved shape to a generally noncurved shape.

These and other embodiments may provide one or more of the following advantages. First, the infusion pump system may be portable so that a user can wear the pump device (e.g., adhered to the user's skin or carried in a user's pocket or portion of clothing) and receive the infused medicine throughout the day or night. Second, the pump device of the infusion pump system may include a drive system that controllably dispenses medicine in a reliable manner. Third, the pump device of the infusion pump system can be removably attached to a controller device having a user interface. As such, the user can readily monitor the operation of the pump device without the need for carrying and operating an separate wireless module. Fourth, some embodiments of the pump device can include a pushrod that is flexible. For example, the pushrod may comprise rod segments interconnected by hinge portions that permit portions of the pushrod to adjust from a curved shape to a generally noncurved shape. Fifth, the pushrod may be equipped with an anti-rotation mechanism that opposes rotation of the pushrod about its longitudinal axis. In these circumstances, the pushrod is hindered from rotating when a drive wheel or the like rotates about the wheel axis. Sixth, the pushrod may be equipped with an anti-torsion mechanism that opposes torsion of one pushrod segment relative to another pushrod segment. Accordingly, the anti-torsion mechanism can oppose the torsion stress across the hinge portions during operation of the drive system. Seventh, the pushrod may be equipped with an anti-elongation mechanism that maintains a portion of the pushrod in a rigid condition after that portion of the pushrod has been adjusted to the generally noncurved shape. Such an anti-elongation mechanism may reduce the likelihood of incidental dispensation of medicine with the pump device undergoes an impact (e.g., when the pump device is dropped on the ground).

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
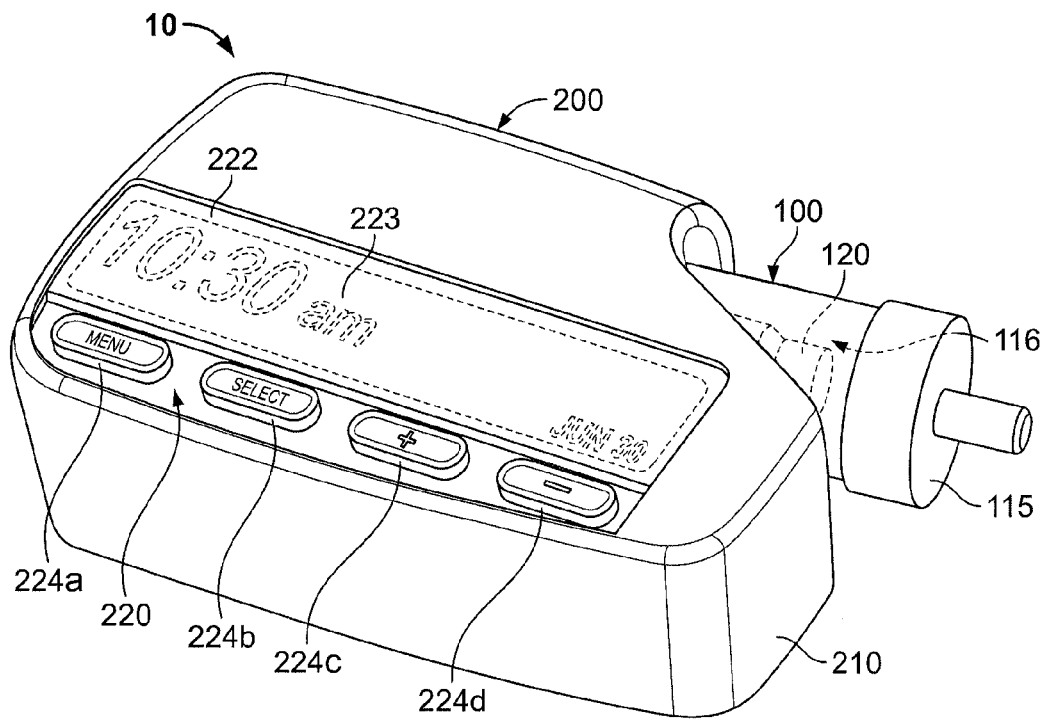
FIG. 1 is a perspective view of an infusion pump system, in accordance with some embodiments.
Figure 2:
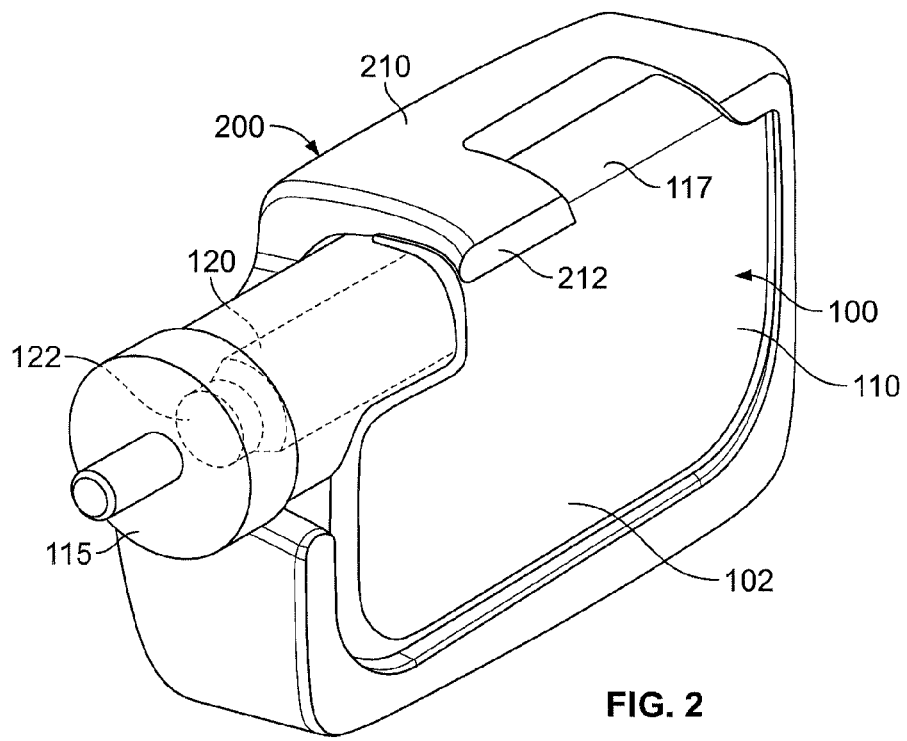
FIG. 2 is another perspective view of the infusion pump system of FIG. 1.

Referring to FIGS. 1-2, some embodiments of an infusion pump system 10 include a pump device 100 that can communicate with a controller device 200. The pump device 100 includes a housing structure 110 that defines a cavity 116 in which a fluid cartridge 120 is received. In this embodiment, the pump system 10 in a medical infusion pump system that is configured to controllably dispense a medicine from the cartridge 120. As such, the fluid cartridge 120 may contain a medicine to be infused into the tissue or vasculature of a targeted individual, such as a human or animal patient. For example, the pump device 100 can be adapted to receive a medicine cartridge 120 in the form of a carpule that is pre-loaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines.

In some embodiments, the controller device 200 may be removably attached to pump device 100 so that the two components are mechanically mounted to one another. Such a mechanical attachment can secure an electrical connection between the removable controller device 200 and the pump device 100. For example, the controller device 200 may be in electrical communication with a portion of a drive system (not shown in FIGS. 1-2) of the pump device 100. As described in more detail below, the pump device 100 includes a drive system that causes controlled dispensation of the medicine or other fluid from the cartridge 120. In some embodiments, the drive system incrementally advances a pushrod (refer, for example, to FIG. 7) longitudinally into the cartridge 120 so that the fluid is force out of the output end 122. In this embodiment, the septum at the output end 122 can be pierced to permit fluid outflow when a cap member 115 is connected to the pump housing structure 110 (described in more detail below, for example, in connection with FIG. 5). Thus, when the pump device 100 and the controller device 200 are removably attached and thereby electrically connected, the controller device 200 communicates electronic control signals via hard-wire-connection to the drive system or other components of the pump device 100. In response to the electrical control signals from the controller device 200, the drive system of the pump device 100 causes medicine to incrementally dispense from the medicine cartridge 120.

Still referring to FIGS. 1-2, The controller device 200 can include a controller housing structure 210 that is configured to mate with a complementary portion of the pump housing structure 110 so as to form a releasable mechanical connection. For example, the controller housing structure 210 may define a cavity (refer, for example, to FIG. 6) that mates with a portion of the pump housing structure 110 for a snap fit engagement. Also, the controller housing structure 210 may include a finger 212 that engages a mating surface 117 of the pump housing structure 110 when the controller device 200 is removably attached to the pump device 100. As described in more detail below in connection with FIGS. 4-5, a magnetic attachment may be employed to releasably secure the pump device 100. For example, the magnetic attachment can serve to retain the pump housing structure 110 in the cavity defined by the controller housing structure 210. In alternative embodiments, one or more releasable connector devices (e.g., mating tongues and grooves, mounting protrusions friction fit into mating cavities, or the like) can be used to further implement the releasable securement of the controller device 200 to the pump device 100.

As described in more detail below in connection with FIGS. 4-5, the pump device 100 may include one or more electrical contacts (e.g., conductive pads, pins, and the like) that are exposed to the controller device 200 and that mate with complementary electrical contacts on the adjacent face of the controller device 200. The electrical contacts provide the electrical communication between the control circuitry of the controller device 200 and at least a portion of the drive system or other components of the pump device 100. For example, in some embodiments, the electrical contacts permit the transmission electrical control signals to the pump device 100 and the reception of feedback signals (e.g., sensor signals) from particular components within the pump device 100.

Still referring to FIGS. 1-2, the controller device 200 includes a user interface 220 that permits a user to monitor the operation of the pump device 100. In some embodiments, the user interface includes a display 222 and one or more user-selectable buttons (e.g., four buttons 224a, 224b, 224c, and 224d in this embodiment). The display 222 may include an active area 223 in which numerals, text, symbols, images, or combination thereof can be displayed. For example, the display 222 may be used to communicate a number of settings or menu options for the infusion pump system 10. In this embodiment, the user may press one or more of the buttons 224a, 224b, 224c, and 224d to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, or the like). As described in more detail below, in some embodiments, the user can adjust the settings or otherwise program the controller device 200 by pressing one or more buttons 224a, 224b, 224c, and 224d of the user interface 220. In embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time.

As shown if FIG. 1, the display 222 of the user interface 220 may be configured to display quick reference information when no buttons 224a, 224b, 224c, and 224d have been pressed. In this example, the active area 223 of the display 222 can display the time and the date for a period of time after no button 224a, 224b, 224c, or 224d has been actuated (e.g., five seconds, 10 seconds, 30 seconds, 1 minute, 5 minutes, or the like). Thereafter, the display 222 may enter sleep mode in which the active area 223 is blank, thereby conserving battery power. In addition or in the alternative, the active area can display particular device settings, such as the current dispensation rate or the total medicine dispensed, for a period of time after no button 224a, 224b, 224c, or 224d has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224a, 224b, 224c, or 224d has been actuated (e.g., after 15 seconds or the like), and then the display 22 can enter sleep mode and become blank after a second period of time in which no button 224a, 224b, 224c, or 224d has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the user interface 220 connected to the pump device 100. Such monitoring capabilities may provide comfort to a user who may have urgent questions about the current operation of the pump device 100 (e.g., the user may be unable to receive immediate answers if wearing an infusion pump device having no user interface attached thereto).

Also, there is no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 removably attached to the pump device 100, without the requirement of locating and operating a separate monitoring module.

It should be understood from the description herein that the user interface 200 is not limited to the display and buttons depicted in FIG. 1. For example, in some embodiments, the user interface 220 may include only one button or may include a numbers of buttons, such as two buttons, three buttons, five buttons, or more. In another example, the user interface 220 of the controller device 200 may include touch screen so that a user may select buttons defined by the active area of the touch screen display. Alternatively, the user interface may comprise audio inputs or outputs so that a user can monitor the operation of the pump device. Previously incorporated U.S. Provisional Application Ser. No. 60/721,267 also describes a number of configurations for a removable controller device and a user interface for the device in addition to the configuration illustrated in FIGS. 1-2 herein.

Figure 3:
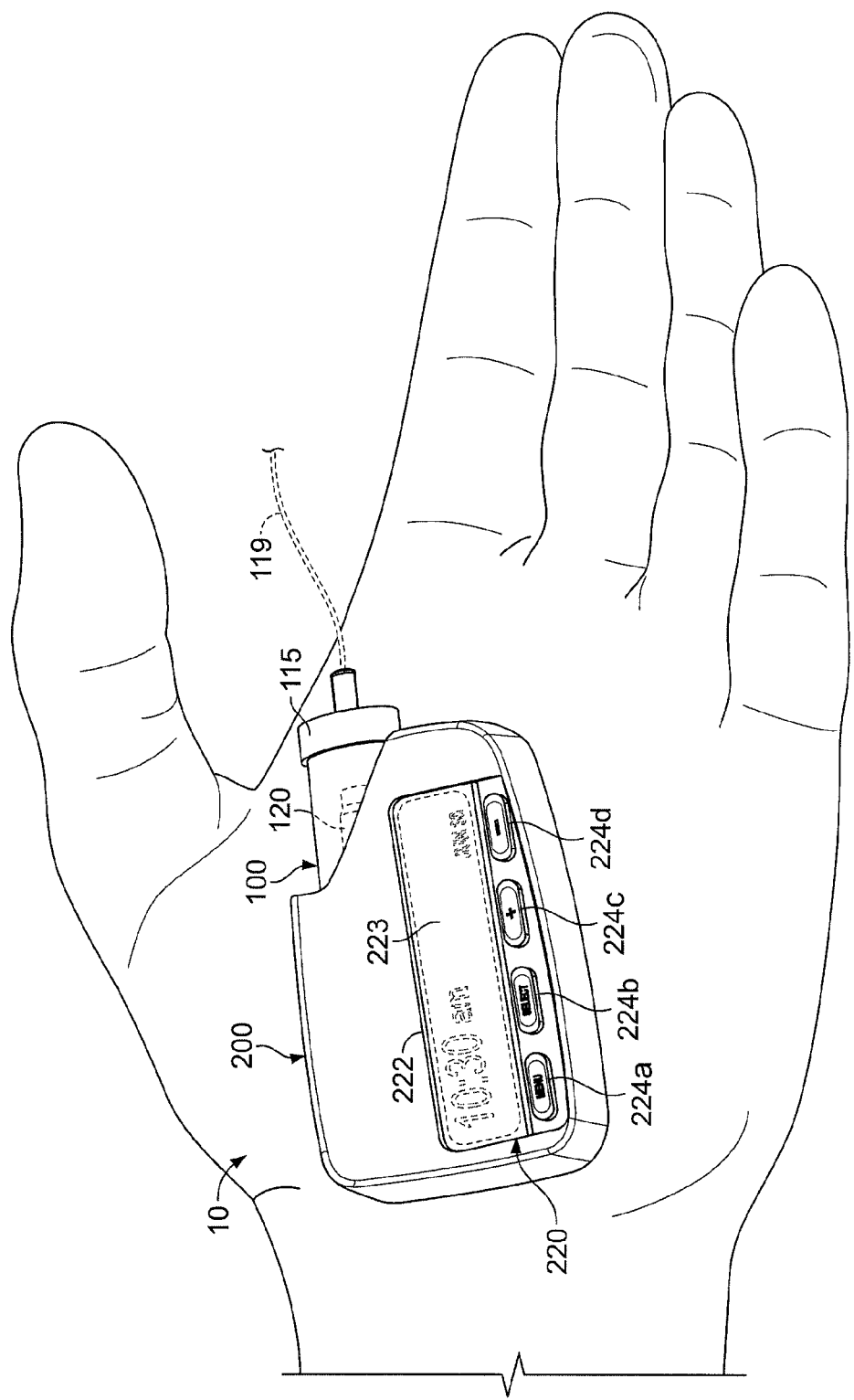
FIG. 3 is another perspective view of the infusion pump system of FIG. 1.

Referring to FIG. 3, the infusion pump system 10 may be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. As described in more detail below, the drive system may be housed in the housing structure 110 of the pump device 100 in a compact manner so that the pump device 100 has a reduced length. For example, in the circumstances in which the medicine cartridge 120 has a length of about 6 cm to about 7 cm (about 6.4 cm in this embodiment), the overall length of the pump housing structure 110 (which contains medicine cartridge and the drive system) can be about 7 cm to about 9 cm (about 8.3 cm or less in this embodiment). In addition, the pump housing structure 110 may have an overall height of about 1.5 cm to about 4 cm (about 2.9 cm or less in this embodiment) and an overall thickness of about 8 mm to about 20 mm (about 14.5 mm or less in this embodiment). In such circumstances, the controller device 200 can be figured to mate with the compact pump housing 110 so that, when removably attached to one another, the components define a portable infusion pump unit that stores a relatively large quantity of medicine compared to the overall size of the unit. For example, in this embodiment, the infusion pump system 10 (including the pump device 100 attached to the removable controller device 200) may have an overall length of about 7 cm to about 9 cm (about 8.5 cm or less in this embodiment), an overall height of about 1.5 cm to about 4 cm (about 3.5 cm or less in this embodiment), and an overall thickness of about 8 mm to about 20 mm (about 15 mm or less in this embodiment).

As shown in FIG. 3, this embodiment of the infusion pump system 10 is pocket-sized so that the pump device 100 and controller device 200 can be worn in the user's pocket or in another portion of the user's clothing. In such embodiments, the cap member 115 of the pump device 100 may be configured to connect with a flexible tube 119 of an infusion set. The infusion set may include the tube 119 that extends toward a skin adhesive patch and connects with an infusion cannula (not shown in FIG. 3). The skin adhesive patch can retain the infusion cannula in fluid communication with the tissue or vasculature of the patient so that the medicine dispensed through the tube 119 passes through the cannula and into the user's body. As described below in connection with FIG. 5, the cap member 115 may provide fluid communication between the output end 122 (FIG. 1) of the medicine cartridge 120 and the tube 119 of the infusion set. In these embodiments, the user can carry the portable infusion pump system 10 (e.g., in the user's pocket, connected to a belt clip, or adhered to the user's skin) while the tube 119 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module.

In other embodiments, the infusion pump system 10 may be configured to adhere to the user's skin directly at the location in which the skin is penetrated for medicine infusion. For example, a rear surface 102 of the pump device 100 (refer, for example, to FIG. 2) may include a skin adhesive patch so that the pump device 100 is physically adhered to the skin of the user at a particular location. In these embodiments, the cap member 115 may have a configuration in which medicine passes directly from the cap member 115 into an infusion cannula that is penetrated into the user's skin. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 220 that is removably attached thereto.

Figure 4:
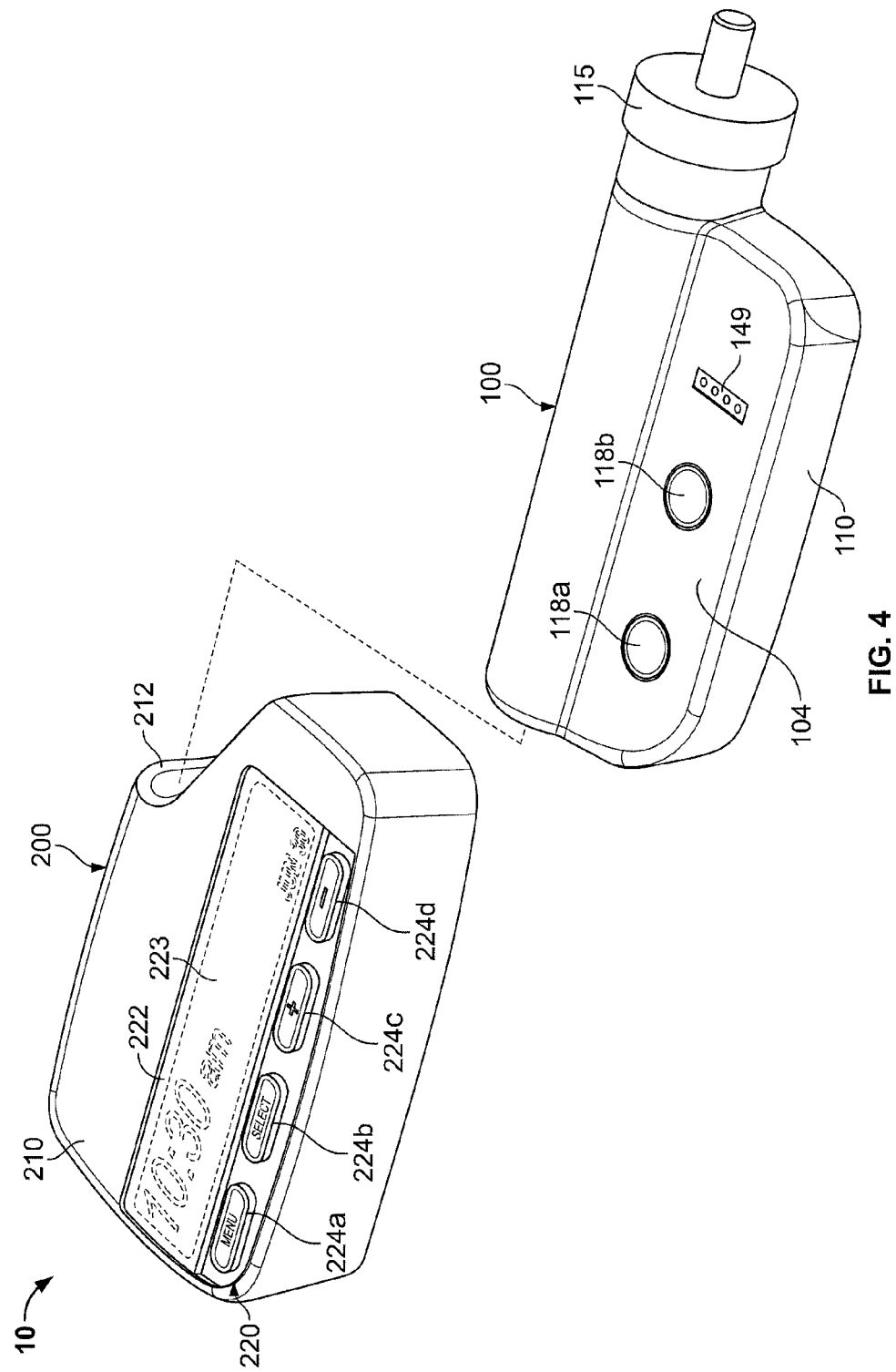
FIG. 4 is an exploded perspective view of the infusion pump system of FIG. 1.
Figure 5:
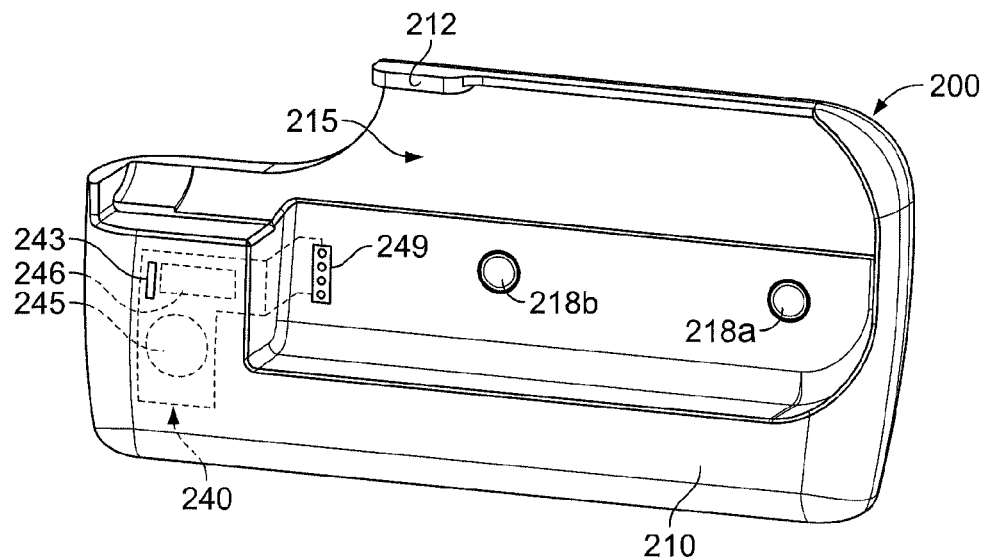
FIG. 5 is a perspective view of a controller device of the infusion pump system of FIG. 1.
Figure 6:
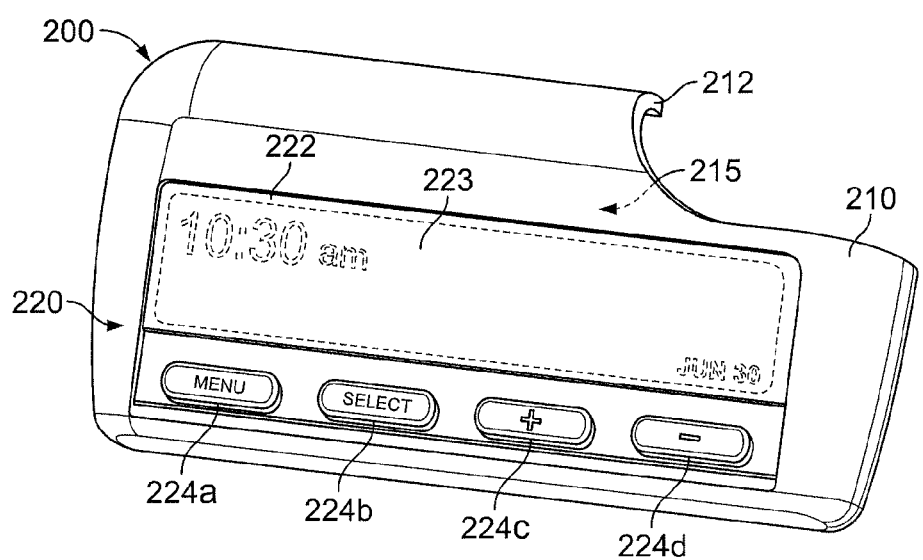
FIG. 6 is a perspective view of one controller device of the infusion pump system of FIG. 5.

Referring to FIGS. 4-6, as previously described, the pump device 100 of the infusion pump system 10 is configured to removably attached to the controller device 200. In this embodiment, the pump device 100 includes a pump housing structure 110, and at least a portion of the pump housing structure 110 is configured to be received in a complementary cavity 215 (FIG. 5) defined in the controller housing structure 210. When the pump device 100 is received by the controller device 200, a retainer finger 212 may engage a mating surface of the pump housing structure 110. In addition, a magnetic attachment can be used to releasably secure the pump device 100 to any of the controller housing structures 210. In such circumstances, the pump device 100 includes one or more magnetically attractable devices 118a and 118b (e.g., permanent magnets in this embodiment depicted in FIG. 4) exhibited on the front surface 104 of the pump housing structure 110 which magnetically engage complementary devices 218a and 218b (e.g., permanent magnets in this embodiment depicted in FIG. 5) arranged on the controller housing structure 210. As such, when the pump device 100 is received in the cavity 215 defined by the controller housing structure 210, the magnetically attractable devices 118a-b and 218a-b form a magnetic attachment to retain the pump device 100 therein.

As shown in FIG. 4, the pump device 100 may include one or more electrical contacts 149 that provide electrical communication with one or more components disposed in the pump device 100. Also, as shown in FIG. 5, the controller device 200 may include one or more electrical contacts 249 that provide electrical communication with one or more components disposed in the controller device 200, such as a controller circuit 240. The electrical contacts 149 of the pump device 100 are arranged to engage complementary electrical contacts 249 (FIG. 5) positioned on the controller housing structure 210. In this embodiment, the electrical contacts 249 are arranged on the controller housing structure 210 so as to align with the electrical contacts 149 of the pump device 100 when the pump device 100 is received in the cavity 215 of the controller device 200. Accordingly, when the pump device 100 is removably attached to the controller device 200, the controller device 200 becomes electrically connected to the pump device 100 via the contacts 149 and 249 to provide for the communication of electrical control signals from the controller circuit 240.

Still referring to FIGS. 4-6, the controller circuit 240 of the controller device 200 may include a battery 245 and a microcontroller device 246 that coordinates the electrical communication to and from the controller device 200. At least a portion of the controller circuit 240 can be embodied on a printed circuit board (or a flexible circuit substrate). The battery 245 and the microcontroller 246 can be mounted to such a printed circuit board (or connect to such a flexible circuit substrate). Electrical connections from the electrical contacts 249 and the user interface 220 (FIG. 6) may extend along the printed circuit board to the microcontroller device 246. In this embodiment, the controller circuit 240 is disposed in a hollow space of the controller housing structure 210. For example, the controller housing structure 210 can be formed from two molded portions that are welded or adhered to one another after the controller circuit 240 is assembled therein. As shown in FIG. 5, some embodiments of the controller circuit 240 may include a cable connector 243 (e.g., a USB connection port or another data cable port). As such, a cable may be connected to the controller circuit 240 to upload data or program settings to the controller circuit or to download data from the controller circuit 240. For example, historical data of medicine delivery can be downloaded from the controller circuit 240 (via the cable connector 243) to a computer system of a physician or a user for purposes of analysis and program adjustments. Optionally, the data cable may also provide recharging power to the controller circuit 240.

Still referring to FIGS. 4-6, the user interface 220 of the controller device 200 can include input components, output components, or both that are electrically connected to the controller circuit 240 (FIG. 5). For example, in this embodiment, the user interface includes a display device 222 having an active area 223 that outputs information to a user and four buttons 224a, 224b, 224c, and 224d that receive input from the user. Here, the display 222 may be used to communicate a number of settings or menu options for the infusion pump system 10. In this embodiment, the controller circuit 240 may receive the input commands from the user's button selection and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). As previously described, the controller circuit 240 can be programmable in that the input commands from the button selections can cause the controller circuit 240 to change any one of a number of settings for the infusion pump system 100.

Optionally, the controller device 200 may include an indicia (not shown in FIGS. 4-6) that identifies the particular type of medicine cartridge 120 or medicine with which it is to be employed. The medicine cartridge 120 may include a similar indicia (not shown in FIGS. 4-6). As such, the user can verify that the appropriate type of medicine is received in the pump device 100 for controlled dispensation by the controller device 200. For example, the indicia may include a label, marking, etching, or the like disposed on the controller housing structure 210 that indicates a particular name, code, or other identifier corresponding to a particular medicine 231 (e.g., "EXENATIDE", "BYETTA", "INSULIN", or another identifier).

Figure 7:
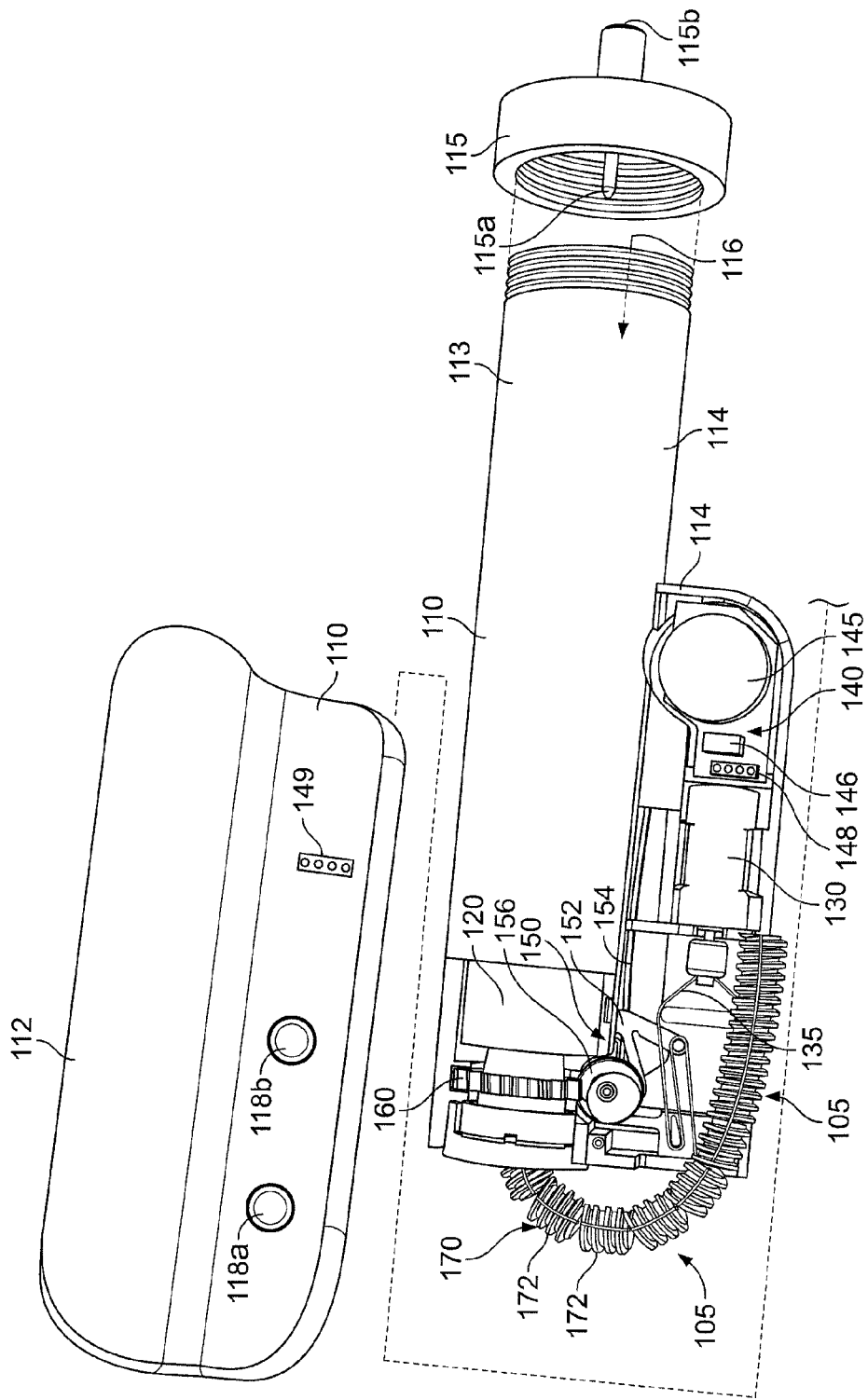
FIG. 7 is an exploded view of a pump device of the infusion pump system of FIG. 1.

Referring now to FIG. 7, the pump device 100 of the infusion pump system 10 may include a drive system 105 that is controlled by the removable controller device 200. Accordingly, the drive system 105 can accurately and incrementally dispense fluid from the pump device 100 in a controlled manner. In this embodiment, the pump housing structure 110 includes a detachable shell 112 that covers at least a portion of the drive system 105 and includes a frame portion 114 to which at least a portion of the drive system 105 is mounted. The detachable shell 112 may include an inner curved surface against which a curved section of a pushrod 170 rests. The detachable shell 112 can be part of the pump housing structure 110 that engages with the controller device 200 as previously described in connection with FIGS. 4-6. As such, the detachable shell portion 112 may include the magnetically attractable devices 118a and 118b that releasably secure the pump device 100 to the controller device 200. In addition, the detachable shell 112 may provide access to the electrical contacts 149 of the pump device 100. In this embodiment, the electrical contacts 149 are configured to align with the contact circuit device 148 arranged in the pump device 100. In other embodiments, the electrical contacts of the pump device 100 can be arranged directly on the contact circuit device 148, and the detachable shell 112 may include a slot (in the location shown as numeral 149) so as to permit electrical engagement with the controller device 200.

One or both of the detachable shell 112 and the frame portion 114 can be molded from polymer material, such as Polycarbonate, Acrylonitrile Butadiene Styrene (ABS), or Acrylic. In this embodiment, the detachable shell portion 112 comprises a generally opaque, moldable material so that the drive system 105 and other components of the pump device are concealed from view. The frame portion 114 may include a cylindrical receiver 113 that defines the space 116 to receive the medicine cartridge 120 (FIG. 2). In some circumstances, at least a portion of the cylindrical receiver 113 is transparent or translucent so that the user may view the medicine cartridge 120 therein. Such a configuration provides the user with visual verification of when the medicine cartridge is empty or near empty (e.g., the plunger in the medicine cartridge has been fully advanced). The receiver 113 may also include a connector to mate with the cap member 115. In this embodiment, the connector comprises an external thread pattern formed on the receiver 113 that mates with an internal thread pattern of the cap member 115. Accordingly, the cap member 115 can be secured to the frame portion 113 after the medicine cartridge 120 (FIG. 2) has been received therein. As shown in FIG. 7, the cap member 115 may include a cartridge penetrator 115a that pierces the output end 122 (FIG. 2) of the medicine cartridge 120 when the cap member 115 is mounted to the frame portion 113. The cartridge penetrator 115a is in fluid communication with an tube connector 115b, which can be connected to a tube 119 of an infusion set device (as previously described in connection with FIG. 3). As previously described, in some embodiments, the fluid cartridge 120 may occupy a majority of the length of the pump housing structure 110 (with the drive system 105 being arranged in a compact manner) so that the pump device 100 is wearable and portable.

Still referring to FIG. 7, some embodiments of the pump device 100 include a local pump circuit 140 that includes the contact circuit device 148. The local pump circuit 140 may be simple and inexpensive so as to facilitate a low-cost pump device 100 that is disposable. The local pump circuit 140 may comprise a printed circuit board or a flexible circuit that is arranged in the frame portion 114 of the pump device 100. Optionally, the local pump circuit 140 can include a gateway circuit device 146 that coordinates the transmission of electrical signals to or from the contact circuit device 148 and to or from components of the drive system 105 (e.g., the motor 130 and other components). In some circumstances, the gateway circuit device 146 may be under the control of and directed by the control circuit 240 in the controller device 200. It should be understood that, in other embodiments, the local pump circuit 140 may be configured to operate without the gateway circuit device 146. For example, the control circuit in the removable controller device 200 may communicate via the electrical contacts directly with a portion of the drive system 105 (e.g., direct electrical communication with the motor 130), with one or more sensors disposed in the pump device 100, and with other components of the local pump circuit 140.

Optionally, the local pump circuit 140 may include a battery 145 that is capable of transmitting electrical energy to the controller device 200 when the pump device 100 is removably attached to the controller device 200. As such, the battery 145 in the pump device can be used to recharge the battery 245 (FIG. 5) in the reusable controller device 200. In some embodiments, the local pump circuit 140 may be electrically connected to one or more sensors disposed in the pump device 100. For example, the gateway circuit device 146 of the circuit 140 may be in electrical communication (e.g., via one or more electrical wires or electrically conductive traces) with a force sensor 147 (refer to FIG. 8) arranged between the plunger connector 178 that the plunger 121. The force sensor 147 may comprise a force transducer or load cell that is capable of electrically communicating an applied force. As such, the force sensor 147 can provide feedback signals to the local pump circuit 140 (or to the control device 200 via the electrical contacts) so as to monitor the force transmitted to the plunger 121 of the medicine cartridge 120. Such information can be used, for example, to detect if an occlusion exists in the medicine flow path. Other sensors (e.g., a pressure sensor, a flow sensor, a rotation sensor, a displacement sensor, or the like) may be electrically connected to the pump circuit 140 to provide feedback signals to the control device 200 via the electrical contacts.

Figure 8:
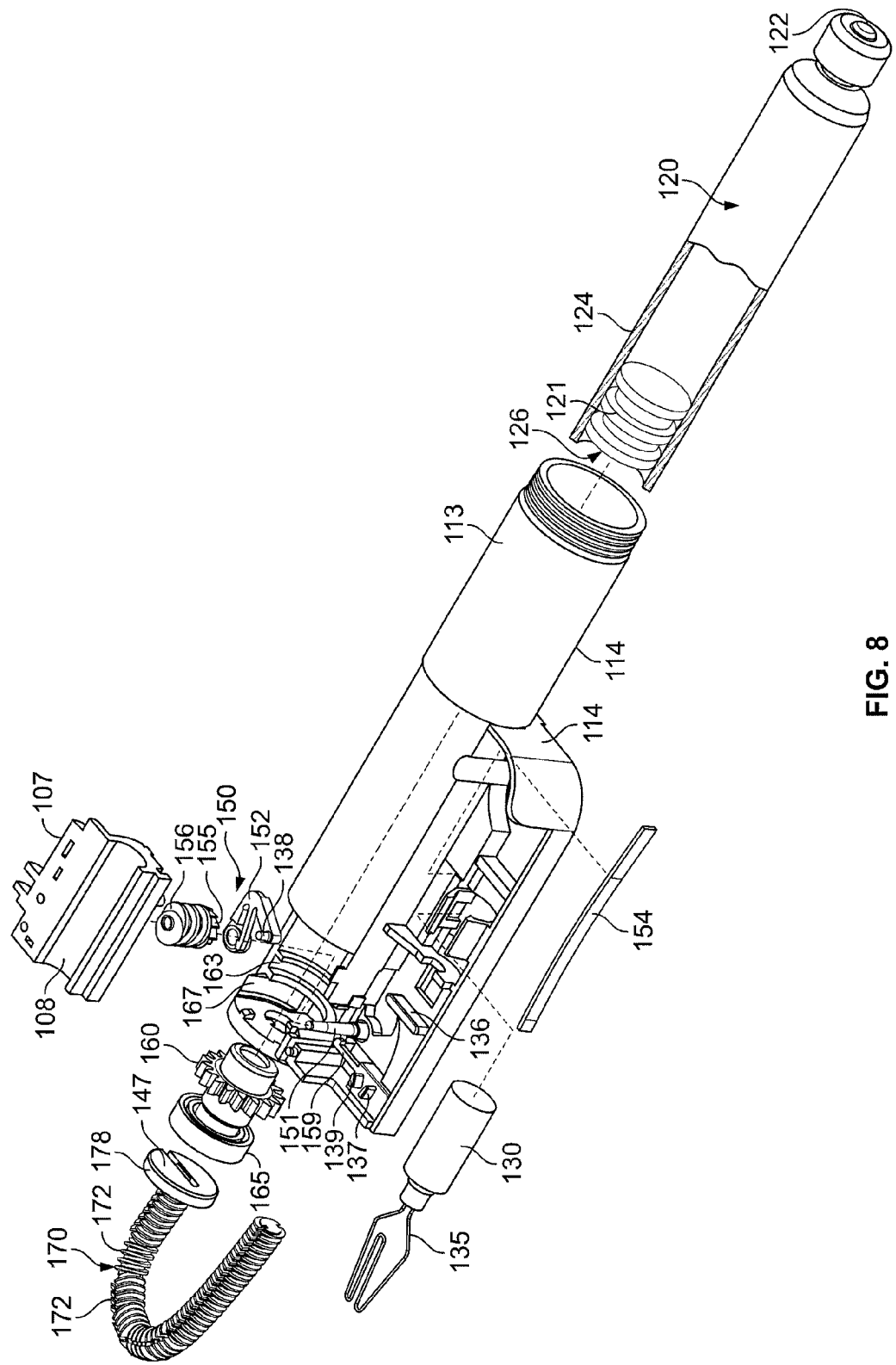
FIG. 8 is an exploded view of a portion of the pump device of the infusion pump system of FIG. 7.

Referring to FIGS. 7-8, some embodiments of the drive system 105 may include a rotational motor 130 that is coupled to a string member 135, which is used to adjust a ratchet mechanism 150. The ratchet mechanism 150 may drive the forward incremental motion of the pushrod 170 so as to dispense medicine from the pump device 100. The drive system 105 can provide a reliable and compact configuration for accurately dispensing the desired volume of fluid from the pump device 100. Moreover, the drive system 105 may comprise few, if any, high-cost actuator components or electronics, thereby facilitating the relatively low-cost production of a disposable and reliable pump device 100.

Referring to the drive system 105 in more detail, the rotational motor 130 can be used to act upon the string member 135, thereby causing the string member 135 to adjust a pawl member 152 relative to a ratchet body 155 (e.g., a ratchet wheel integrally formed on the worm gear 156 in this embodiment). In this embodiment, the string member 135 is configured in a loop arrangement (e.g., looped around pin structures 136, 137, 138, and 139 in this embodiment) so that the string member 135 can be twisted or untwisted in response to the motor rotation. In these embodiments, the motion path of the string member 135 and the orientation of the string member 135 can be configured to provide an efficient mechanical advantage orientation during the desired motion of the adjustable pawl member 152. One of the pin structures 138 may be coupled to the adjustable pawl member 152 while the remaining pin structures 136, 137, and 139 are coupled to the frame portion 114 of the pump device 100. Accordingly, the motor 130 can twist the string to force the pawl member 152 to a reset position. The spring device 154 can drive the pawl member from the reset position to a forward position (as the string member is untwisted), which incrementally rotates the ratchet wheel 155. As previously described, incremental rotation of the ratchet wheel 155 causes rotation of a drive wheel 160, which causes the incremental longitudinal advancement of a flexible pushrod 170. A plunger connector 178 may be coupled to the leading end of the flexible pushrod 170 so as to abut against or connect with the plunger 121 in the plunger chamber 126 of the fluid cartridge 120. As the pushrod 170 is advanced into plunger chamber 126 (e.g., defined in this embodiment by the circumferential wall 124 of the fluid cartridge 120), the fluid in the cartridge 120 is forced from septum at the output end 122.

As shown in FIG. 8, some components of the drive system 105 can be retained by the frame portion 114, a cover mount 107 that is assembled to the frame portion 114, or a combination thereof. For example, the rotational motor 130, the string member 135, and the spring device 154 can be assembled into the frame portion 114 and then retained by the cover mount 107. The adjustable pawl member 152, the ratchet wheel 155, and the worm gear 156 can be assembled onto and axle 151 that is integrally formed with the frame portion 114 and then retained by the cover mount 107. A locking pawl 159 can be integrally formed with the frame portion 114 so as to align with the ratchet wheel 155 when the ratchet wheel 155 is assembled onto the axle 151. Also, the drive wheel 160 and an adjacent bearing 165 (to facilitate rotation of the drive wheel 160 relative to the frame portion 114) can be received in annular channels 163 and 167, respectively, of the frame portion 114. When the cover mount 107 is assembled to the frame portion 114, the cover mount 107 can restrict the radial or axial movement of the drive wheel 160 while permitting forward rotation of the drive wheel 160. In another example, the "unused" or retracted portion of the pushrod 170 may rest in a channel 108 defined in the top of the cover mount 107. In such a construction, the cover mount 107 and the frame portion 114 can collectively permit the desired motion of the components of the drive system 105 while reducing the likelihood of "backlash" movement or component dislodgement (which might otherwise occur, for example, when the pump device 100 is dropped to the ground). Previously incorporated U.S. Provisional Application Ser. No. 60/720,411 also describes a number of configurations for the drive system in addition to the illustrative example depicted in FIG. 8 herein.

It should be understood that the drive system 105 can employ one or more sensors to indicate when the pawl member 152 has reach the reset position or the forward position. For example, these sensors can be optical, magnetic, or contact type sensors. The sensors may be capable of transmitting signals that indicate when the location of the pin structure 148 or the pawl member 152 is detected. Such sensor signals may be transmitted to the first circuit 140, to the controller device 200 or 300, or a combination thereof.

In some embodiments, the pushrod 170 may undergo only forward or positive displacement as a result of drive system 105. For example, the drive system 105 substantially hinders the pushrod 170 from retracting or "backing up" in response to fluid pressure in the medicine cartridge 120 or other reversal forces. In such circumstances, the flexible pushrod 170 can be retracted only upon disassembly of the pump device 100 (e.g., to disengage the gears or the ratchet mechanism). In those embodiments in which the pump device 100 is intended to be disposable, the non-retractable pushrod configuration (due to the drive system 105) may facilitate a "one time use" disposable pump device, thereby reducing the likelihood of failure due to non-intended repeated use of the disposable pump device.

Figure 9:
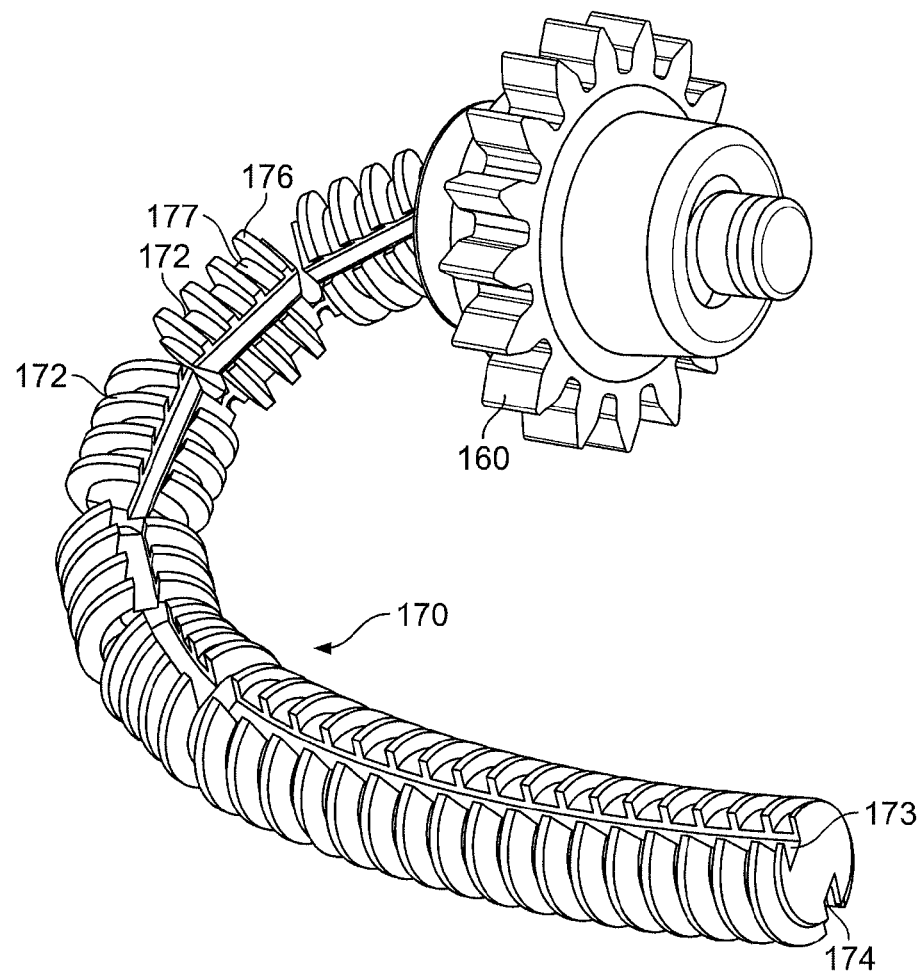
FIG. 9 is a perspective view of a portion of a drive system of the pump device of FIG. 8.
Figure 10:
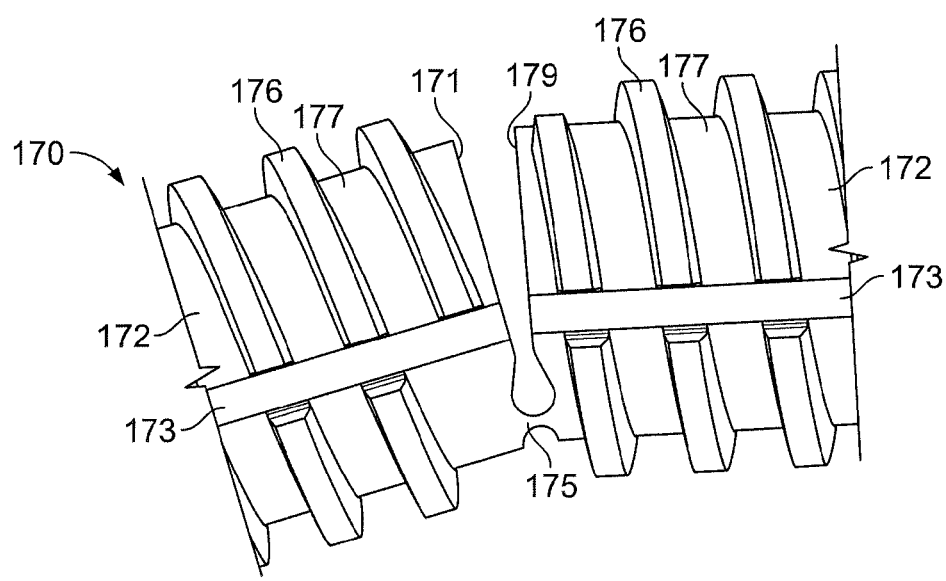
FIG. 10 is a perspective view of a portion of a flexible pushrod of the drive system of FIG. 9.

Referring to FIGS. 9-10, the flexible pushrod 170 may comprise a plurality of segments 172 serially connected by hinge portions 175 so that the flexible pushrod 170 is adjustable from a curved shape to a noncurved shape. The plurality of segments 172 and the interconnecting hinge portions 175 (FIG. 10) can be integrally formed in one piece from a moldable material, including one or more polymer materials such as Nylon or POM. As shown in FIG. 10, each segment 172 is hingedly engaged with the adjacent, neighboring segment 172. Thus, each segment 172 can pivot away from the adjacent segment 172 so that a portion the flexible pushrod 170 takes on a curved shape. Also, each segment can pivot toward the adjacent segments so that a front surface or leading face 171 of one segment abuts the rear surface or trailing face 179 of the adjacent segment 179, thereby forming a generally noncurved shape for a portion of the pushrod 170. When the leading face 171 of one segment 172 abuts the trailing face 179 of the adjacent surface, that portion of the pushrod can become a rigid device to transfer a pushing force.

In this embodiment, the plurality of segments 172 comprise generally cylindrical segments that each include an thread pattern 176 along at least one cylindrical surface portion 177 (FIG. 10). As described in more detail below, the thread pattern 176 can engage a mating thread pattern of the drive wheel 160. For example, the thread pattern 176 of the pushrod segments 172 may be an external thread pattern that mates with an internal thread pattern of the drive wheel 160. Accordingly, the incremental rotation of the drive wheel 160 can be translated into an incremental longitudinal motion for the pushrod 170. Previously incorporated U.S. Provisional Application Ser. No. 60/720,405 also describes a number of configurations for the flexible pushrod and the engagement with the drive wheel.

Still referring to FIGS. 9-10, the flexible pushrod 170 can include an anti-rotation mechanism that hinders the pushrod 170 from rotating with drive wheel 160. In this embodiment, the anti-rotation mechanism includes two longitudinal channels 173 and 174 that engage respective protrusions on the frame portion 114 (refer to FIG. 12), thereby hindering rotation of the pushrod 170 about its longitudinal axis. Because the drive wheel 160 can rotate relative to the pushrod 170 (which is substantially prevented from rotating by the anti-rotation mechanism), the rotation of the drive wheel 160 can thereby translate into the longitudinal motion of the pushrod 170.

Figure 11:
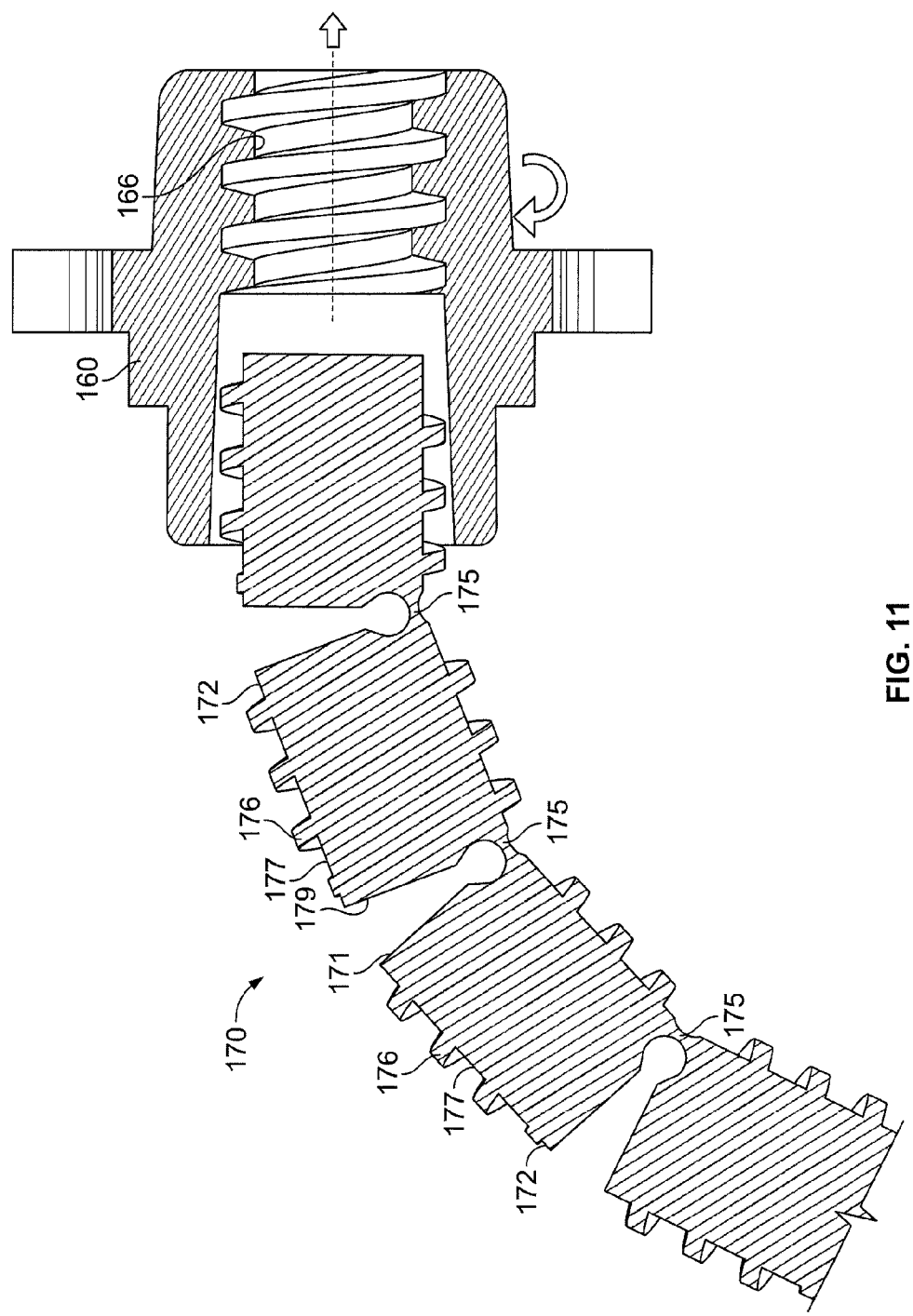
FIG. 11 is a cross-sectional view of the portion of the drive system of FIG. 9.

Referring now to FIG. 11, the flexible pushrod 170 can include a structure that mates with the drive wheel 160 so as to translate the rotation of the drive wheel 160 into a longitudinal motion of the pushrod 170. In this embodiment, the pushrod segments 172 include an external thread pattern 176 along some or all of the cylindrical surface portion 177. The external thread pattern 176 is capable of mating with an internal thread pattern 166 of the drive wheel 160. As such, rotation of the drive wheel 160 causes the internal thread pattern 166 to mesh with external thread pattern 176 of the pushrod segment, thereby driving the pushrod segment in a longitudinal direction. The thread count and angulation of the thread patterns 166 and 176 can be selected to provide predetermined longitudinal advancement distance of the pushrod 170 for a given increment of rotation of the drive wheel 160. In one example, the drive system 105 can advance the pushrod 170 a longitudinal advancement distance of about 16 microns or less (about 4 microns to about 12 microns, and preferably about 7 microns to about 8 microns) for each incremental motion cycle of the motor 130, string member 135, and ratchet mechanism 150 as described herein As shown in FIG. 11, at least a portion of the pushrod 170 that is not yet advanced into engagement with the drive wheel 160 may have a curved shaped. For example, the hinge portions 175 may be flexed so that a first segment 172 is pivoted away from the an adjacent second segment 172. When a segment 172 is forwardly advanced so as to engage the drive wheel 160, that particular segment 172 may hingedly adjust toward the immediately forward segment 172. As such, at least a portion of the pushrod 170 that is advanced through the drive wheel 160 may have a generally straight shape (with the forward most segment 172 pressing against the plunger connector 178 (FIG. 8) that presses against the plunger 121 of the medicine cartridge 120 (FIG. 8)). As previously described, when the portion of the pushrod 170 has a generally straight shape, the leading face 171 of one segment 172 can abut the trailing face 179 of the adjacent segment 174 so as to transfer a pushing force.

Figure 12:
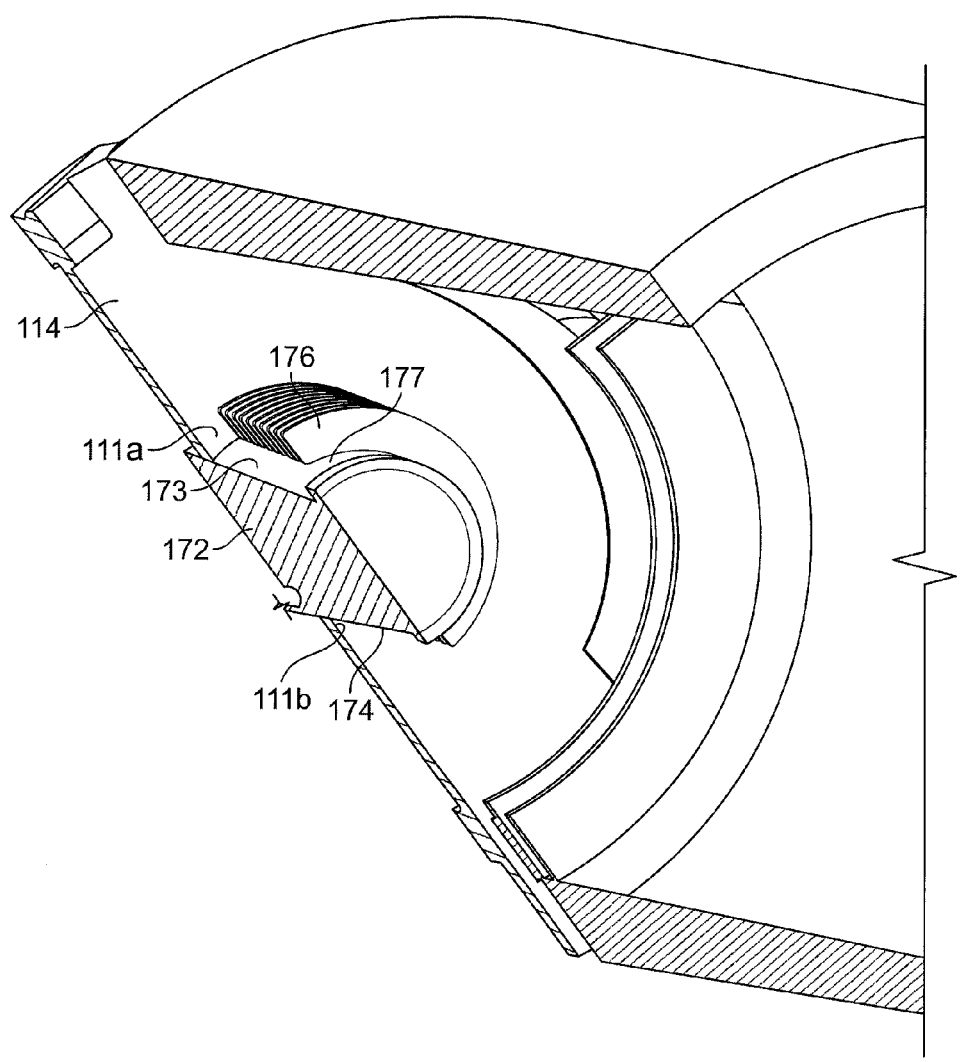
FIG. 12 is a section view of a portion of the pump device of FIG. 8.

Referring to FIG. 12, the anti-rotation mechanism of the flexible pushrod 170 can interact with the frame portion 114 of the pump device 100 so as to hinder rotation of the pushrod 170 during rotation of the drive wheel 160 (removed from FIG. 12 for purposes of illustration; refer to FIG. 8). In such circumstances, the drive wheel 160 can rotate about its axis while the anti-rotation mechanism opposes rotation of the pushrod 170 about the longitudinal axis of the pushrod 170. As previously described, in this embodiment, the anti-rotation mechanism comprises two longitudinal channels 173 and 174, each of which extend through the pushrod segments 172 in a generally longitudinal direction. As shown in FIG. 12, the first longitudinal channel 173 can engage a complementary protrusion 111a on the frame portion 114 proximate the drive wheel 160 (not shown in FIG. 12) so that the flexible pushrod 170 is hindered from rotating when the drive wheel 160 turns relative to the frame portion 114. In addition, the second longitudinal channel 174 can engage a complementary protrusion 111b on the frame portion 114 proximate the drive wheel so as to further hinder rotation of the pushrod 170 when the drive wheel 160 turns relative to the frame portion 114. Accordingly, each longitudinal channel 173 and 174 in the segment 172 aligns to form a keyway that receives a mating key (e.g., the protrusion 111a or 111b) on the frame portion 114.

Accordingly, two or more longitudinal channels (oppositely disposed channels 173 and 174 in this embodiment) may be employed in an anti-rotation mechanism for the pushrod 170. When two channels are employed (rather than a single channel), the channels may be configured to have a relatively smaller size while still providing the anti-rotation services. The smaller-sized channels may permit the pushrod segment 172 to slidably engage the protrusions 111a and 111b of the frame member 114 with substantially reduced friction. Such a reduction in the friction upon the pushrod 170 can reduce the overall load imposed upon the drive system 105 of the pump device.

It should be understood that, as described in more detail below, the anti-rotation mechanism may include one longitudinal channel, three longitudinal channels, or more longitudinal channels (with each channel capable of engaging an associated protrusion that acts as a key to hinder rotation while permitting longitudinal motion). Alternatively, as described in more detail below, the anti-rotation mechanism may include one or more flat surfaces along each segment 172 (with the flat surface slidably engaging a complementary flat surface on the frame portion 114).

Figure 13A:
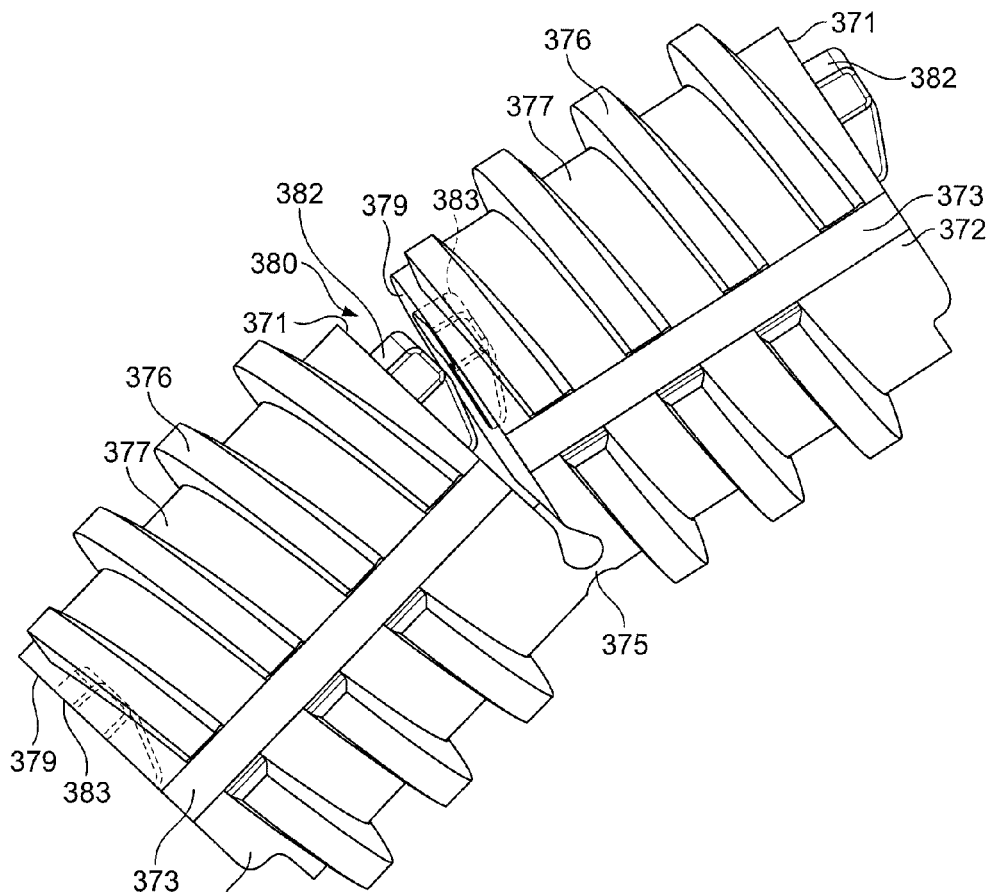
FIGS. 13A-B is a perspective view of a portion of a flexible pushrod in accordance with some embodiments.
Figure 13B:
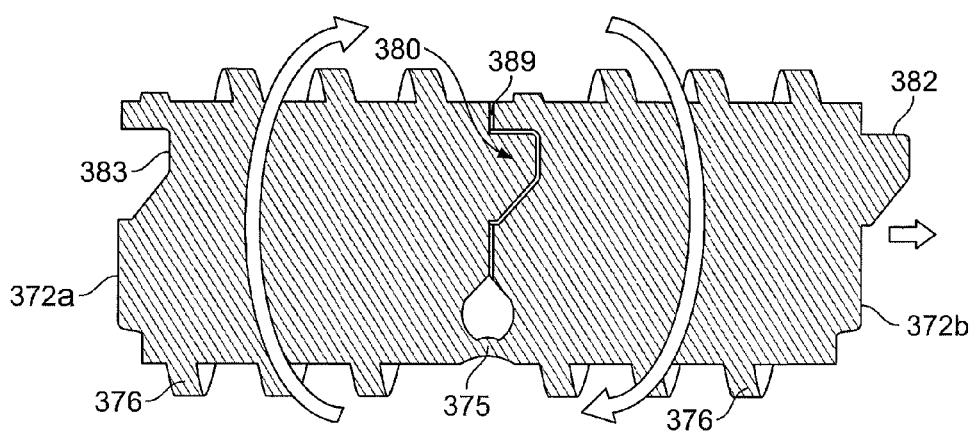

Referring now to FIGS. 13A-B, some embodiments of a flexible pushrod 370 for use in the pump device 100 may include an anti-torsion mechanism 380 and, optionally, an anti-rotation mechanism (e.g., at least one longitudinal channel 373 in this embodiment). Similar to previously described embodiments, the flexible pushrod 370 may comprise a plurality of segments 372 (only two of the segments 372 are shown in FIG. 13 for purposes of illustration) serially connected by hinge portions 375 so that the flexible pushrod 370 is adjustable from a curved shape to a noncurved shape. Thus, each segment 372 can pivot toward or away from the adjacent segment 372 so that a portion the flexible pushrod 370 takes on a curved shape or a noncurved shape. As shown in FIG. 13B, the anti-torsion mechanism 380 may oppose torsion of one rod segment 372 relative to its adjacent rod segment 372. By opposing such torsion, the anti-torsion mechanism 380 can resist the torsion across the hinge portions 375 that would otherwise occur from the twisting motion of one segment 372a relative to the adjacent segment 372b.

Similar to previously described embodiments, the plurality of segments 372 may comprise a thread pattern 376 along at least one cylindrical surface portion 377, and the thread pattern 376 is configured to engage a mating thread pattern of the drive wheel (e.g., similar to drive wheel 160 depicted in FIGS. 8 and 11). Accordingly, the incremental rotation of the drive wheel 160 (FIG. 8) can be translated into an incremental longitudinal motion for the pushrod 370. As previously described, when a segment 372 is forwardly advanced through the drive wheel 160, the segment 372 adjusts toward the immediately forward segment 372 so that a leading face 371 of one segment 372 abuts the trailing face 379 of the adjacent segment 372.

Referring to FIG. 13B, in some circumstances, the rotation of the drive wheel 160 may urge the currently engaged segment 372a to twist relative to the forward segment 372b that is substantially rigidly pressed against the piston connector 178 (FIG. 8) and the piston 121 (FIG. 8). This twisting bias of the rearward segment 372s relative to the adjacent forward segment 372b may create a torsion (refer, for example, to the illustrative arrows in FIG. 13B) across the interconnecting hinge portion 375. Accordingly, the pushrod 370 may be equipped with an anti-torsion mechanism 380 to resist such relative torsion. The anti-torsion mechanism 380 can include an extension member (e.g., member 382) that extends from one segment into a mating cavity (e.g., cavity 383) of the adjacent segment when the two segments are adjusted to a generally straight or rigid condition. For example, in this embodiment, the anti-torsion mechanism 380 may include an integrally formed protrusion 382 that extends from the leading face 371 of a first segment 372. Also in this embodiment, the anti-torsion mechanism 380 includes a cavity 383 formed in the trailing face 379 of a second adjacent segment 372. As shown in FIG. 13B, the cavity 383 is configured to mate with the protrusion 382 when this portion of the pushrod 370 is adjusted to a rigid condition in which the leading face 371 of the first segment 372a abuts with the trailing face 379 of the adjacent forward segment 372b.

Such an engagement of the components of the anti-torsion mechanism 380 enables the flexible pushrod 370 to hinder the twisting motion of the first segment 372a relative to the adjacent segment 372b. Accordingly, the anti-torsion mechanism may oppose torsion of one rod segment 372 relative to its adjacent rod segment 372. By opposing such torsion, the anti-torsion mechanism 380 can resist the torsion across the hinge portions 375 that would otherwise occur from the twisting motion of one segment 372a relative to the adjacent segment 372b.

Optionally, in addition to the anti-torsion mechanism 380, the flexible pushrod 370 can include an anti-rotation mechanism that hinders the pushrod 370 from rotating with drive wheel 160. Thus, while the anti-rotation mechanism hinders rotation of the pushrod 370 relative to the frame portion 114 (e.g., rotation with the drive wheel 160), the anti-torsion mechanism 380 can resist torsion one pushrod segment 372a relative to an adjacent segment 372b. In this embodiment, the anti-rotation mechanism includes two longitudinal channels (only one channel 373 is shown in the view in FIG. 13A) that engage respective protrusions on the frame portion 114 (as previously described in connection with FIG. 12). Because the drive wheel 160 can rotate relative to the pushrod 370 (which is substantially prevented from rotating by the anti-rotation mechanism), the rotation of the drive wheel 160 can thereby translate into the longitudinal motion of the pushrod 370.

Referring again to FIG. 13B, some embodiments of the flexible pushrod 370 for use in the pump device 100 may include an anti-elongation mechanism 379 to maintain the pushrod segments 372 in an abutting relationship after adjusting to the rigid and generally non-curved shape. For example, the anti-elongation mechanism 379 may comprise a pressure-sensitive adhesive disposed on the trailing face 379 of the pushrod segments 372, on the leading face 371 of the pushrod segments 372, or on both the leading and trailing faces 371 and 379 of the pushrod segments 372. Accordingly, when the trailing segment 372a is pivoted about the hinge portion 375 toward the forward segment 372b, the pushrod segments 372a and 372b abut against one another and are maintained in the abutted condition by the pressure-sensitive adhesive 389. Because the segments 372a and 372b are urge in the longitudinal direction toward the piston 121 in the medicine cartridge 120, the pressure between the segments 372a and 372b is sufficient to activate the pressure-sensitive adhesive 389. Also, in some embodiments, the pressure sensitive adhesive may serve as an anti-torsion mechanism that opposes torsion of one rod segment 372a relative to its adjacent rod segment 372b.

Such an engagement of the first segment 372a relative to the adjacent segment 372b serves to hinder elongation of the portion of the pushrod 370 that is being forced against the plunger 121. If, for example, the pump device 100 was dropped on the ground, the plunger 121 in the medicine cartridge may be maintained in a substantially stationary position relative to the pushrod 370 because the pushrod segments 372a and 372b are maintained in the rigid and generally non-curved shape. If the portion of the pushrod 370 that is being pushed against the plunger 121 is permitted to elongate (e.g., if the segments 372a and 372b in FIG. 13B shift to the disengaged orientation shown in FIG. 13A), the plunger 121 may possibly shift inside the medicine cartridge 120 and incidentally dispense some medicine. Accordingly, the anti-elongation mechanism may maintain of the pushrod segments 372a and 372 in the abutting relationship after that portion of the pushrod 370 has been adjust to the rigid and generally non-curved shape.

It should be understood that the anti-elongation mechanism is not limit to the pressure-sensitive adhesive 389 depicted in FIG. 13B. For example, the anti-elongation mechanism may by incorporated into the anti-torsion mechanism 380 (FIG. 13A). In such embodiments, the anti-elongation mechanism may comprise one or more geometric structures (e.g., a hemispherical extension or the like) that extends from one or both of the lateral sides of the protrusion 382 as to snap into and lock with a mating socket (e.g., a corresponding hemi-sperical socket) defined in the cavity 383. In an alternative embodiment, the anti-elongation mechanism may comprise a pressure sensitive adhesive (like adhesive 389 in FIG. 13B) that is disposed on the protrusion 382 of the anti-torsion mechanism 380, on the surface of the cavity 382 of the anti-torsion mechanism 380, or both. In these embodiments, anti-elongation mechanism can maintain of the pushrod segments 372a and 372 in the abutting relationship after that portion of the pushrod 370 has been adjust to the rigid and generally non-curved shape.

Figure 14:
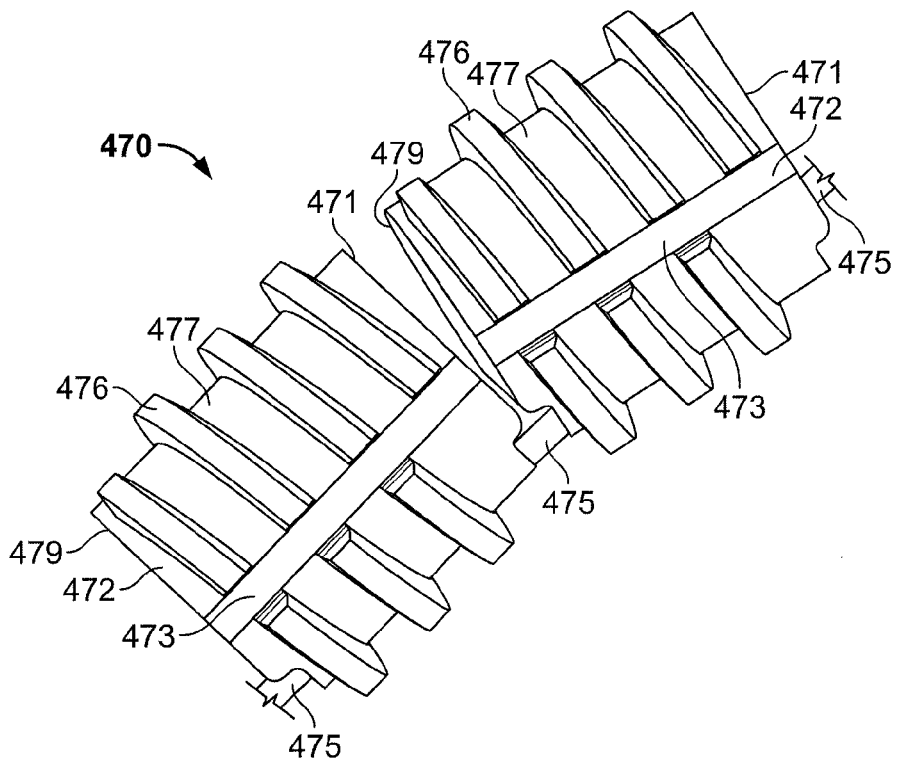
FIG. 14 is a perspective view of a portion of a flexible pushrod in accordance with some embodiments.

Referring now to FIG. 14, some embodiments of a flexible pushrod 470 for use in the pump device 100 may include hinge portions 475 that are not integral with the material of the pushrod segments 472. For example, in this embodiment, the hinge portions 475 may comprise a flexible wire that is integrally molded with or assembled into the segments 472 of the pushrod 470. Similar to previously described embodiments, the flexible pushrod 470 comprises a plurality of segments 472 (only two of the segments 472 are shown in FIG. 14 for purposes of illustration) serially connected by the hinge portions 475 so that the flexible pushrod 470 is adjustable from a curved shape to a noncurved shape. Because the hinge portions comprise a flexible wire configuration, each segment 472 can pivot toward or away from the adjacent segment 472 so that a portion the flexible pushrod 470 takes on a curved shape or a noncurved shape.

Similar to previously described embodiments, the plurality of segments 472 may comprise a thread pattern 476 along at least one cylindrical surface portion 477. The thread pattern 476 is configured to engage a mating thread pattern of the drive wheel (e.g., similar to drive wheel 160 depicted in FIGS. 8 and 11). Accordingly, the incremental rotation of the drive wheel 160 (FIG. 8) can be translated into an incremental longitudinal motion for the pushrod 470. As previously described, when a segment 472 is forwardly advanced through the drive wheel 160, the segment 472 adjusts toward the immediately forward segment 472 so that a leading face 471 of one segment 472 abuts the trailing face 479 of the adjacent segment 472. Optionally, the flexible pushrod 470 can include an anti-rotation mechanism that hinders the pushrod 470 from rotating with drive wheel 160 (FIG. 8). In this embodiment, the anti-rotation mechanism includes two longitudinal channels (only one channel 473 is shown in the view in FIG. 14) that engage respective protrusions on the frame portion 114 (as previously described in connection with FIG. 12).

Still referring to FIG. 14, the plurality of segments 472 can be formed from a moldable material, including one or more polymer materials such as Nylon or POM. During the molding process, a flexible wire comprising a metallic material (e.g., stainless steel, superelastic Nitinol material, or the like) can be placed into the mold. As such, the metallic wire can be integrally molded with the pushrod segments 472 so as to form a one-piece flexible pushrod 470. In such embodiments, the pushrod segments 472 are interconnected by hinge portions 475 that include the flexible wire material. In this embodiment, the hinge portions 475 between the plurality of segments 472 in the pushrod include the same flexible wire piece. It should be understood that, in some embodiments, each individual hinge portion may include an individual flexible wire that is separate from other hinge portions 475 of the pushrod 470.

In some embodiments, the flexible pushrod 470 may include an anti-elongation mechanism that maintains of the pushrod segments 472 in an abutting relationship after that portion of the pushrod 470 has been adjust to the rigid and generally non-curved shape. For example, similar to the embodiments previously described in connection with FIG. 13B, the anti-elongation mechanism may comprise a pressure-sensitive adhesive disposed on the trailing face 479 or leading face 471 of the pushrod segments 472.

Figure 15:
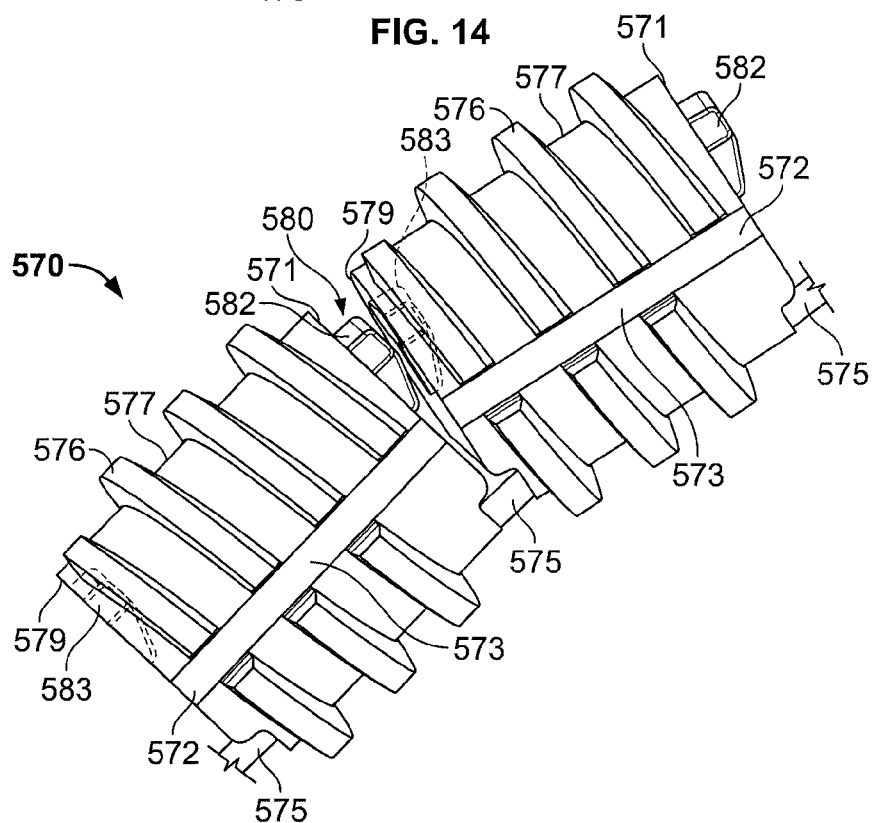
FIG. 15 is a perspective view of a portion of a flexible pushrod in accordance with some embodiments.

Referring now to FIG. 15, some embodiments of a flexible pushrod 570 for use in the pump device 100 may include hinge portions 575 that include a flexible wire material and may include an anti-torsion mechanism 580. Similar to embodiments previously described in connection with FIGS. 13A-B, the anti-torsion mechanism 580 may resist the torsion across the hinge portions 575 that would otherwise occur from the twisting motion of one segment 572 relative to the adjacent segment 572.

In this embodiment, the hinge portions 575 comprise a flexible wire that is integrally molded with or assembled into the segments 572 of the pushrod 570. A plurality of the pushrod segments 572 (only two of the segments 572 are shown in FIG. 15 for purposes of illustration) serially connected by the hinge portions 575 so that the flexible pushrod 570 is adjustable from a curved shape to a noncurved shape. Similar to previously described embodiments, the plurality of segments 572 may comprise a thread pattern 576 along at least one cylindrical surface portion 577. The thread pattern 576 is configured to engage a mating thread pattern of the drive wheel (e.g., similar to drive wheel 160 depicted in FIGS. 8 and 11). Accordingly, the incremental rotation of the drive wheel 160 (FIG. 8) can be translated into an incremental longitudinal motion for the pushrod 570.

As shown in FIG. 15, the pushrod 570 may be equipped with an anti-torsion mechanism 580 to resist relative twisting motion between adjacent segments 572. Similar to embodiments previously described in connection with FIGS. 13A-B, the anti-torsion mechanism 580 can include an integrally formed protrusion 582 that extends from the leading face 571 of a first segment 572. Also in this embodiment, the anti-torsion mechanism 580 also includes a cavity 583 formed in the trailing face 579 of a second adjacent segment 572. The cavity 583 is configured to mate with the protrusion 582 when this portion of the pushrod 570 is adjusted to a rigid condition in which the leading face 571 of the first segment 572 abuts with the trailing face 579 of the adjacent forward segment 572. As previously described, such an engagement of the components of the anti-torsion mechanism 580 enables the flexible pushrod 570 to hinder the twisting motion of the first segment 572 relative to the adjacent segment 572. Accordingly, the anti-torsion mechanism 580 may oppose torsion of one rod segment 572 relative to its adjacent rod segment 572. By opposing such torsion, the anti-torsion mechanism 580 can resist the torsion stresses that might ordinarily occur across the hinge portion 575.

Optionally, in addition to the anti-torsion mechanism 580, the flexible pushrod 570 can include an anti-rotation mechanism that hinders the pushrod 570 from rotating with drive wheel 160 (FIG. 8). In this embodiment, the anti-rotation mechanism includes two longitudinal channels (only one channel 573 is shown in the view in FIG. 15) that engage respective protrusions on the frame portion 114 (as previously described in connection with FIG. 12). Because the drive wheel 160 can rotate relative to the pushrod 570 (which is substantially prevented from rotating by the anti-rotation mechanism), the rotation of the drive wheel can thereby translate into the longitudinal motion of the pushrod 570.

In some embodiments, the flexible pushrod 570 may include an anti-elongation mechanism that maintains of the pushrod segments 572 in an abutting relationship after that portion of the pushrod 570 has been adjust to the rigid and generally non-curved shape. For example, similar to the embodiments previously described in connection with FIG. 13B, the anti-elongation mechanism may comprise a pressure-sensitive adhesive disposed on the trailing face 579 or leading face 571 of the pushrod segments 572 or may be incorporated into the anti-torsion mechanism 580.

Figure 16:
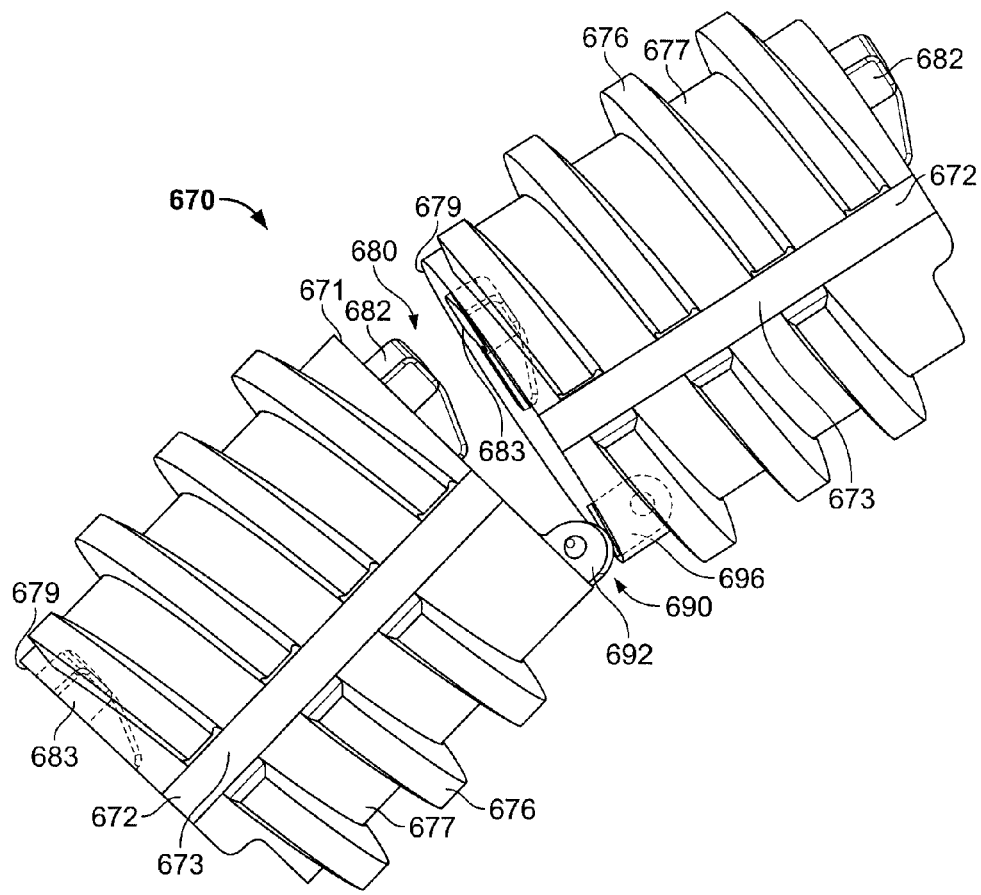
FIG. 16 is a perspective view of a portion of a flexible pushrod in accordance with some embodiments.

Referring to FIG. 16, some embodiments of a flexible pushrod 670 for use in the pump device 100 may include hinge portions 690 that can be assembled to interconnect pushrod segments 672. For example, in this embodiment, the hinge portions 690 may comprise a snap hinge assembly that includes a hinge protrusion 692 (FIGS. 16 and 17A) on one segment 672 connectable with a receiver cavity 696 (FIGS. 16 and 17B) on an adjacent segment 672. The plurality of segments 672 (only two of the segments 672 are shown in FIG. 16 for purposes of illustration) serially connected by the respective snap hinge assemblies 690 so that the flexible pushrod 670 is adjustable from a curved shape to a noncurved shape. Similar to previously described embodiments, the plurality of segments 672 may comprise a thread pattern 676 along at least one cylindrical surface portion 677. The thread pattern 676 is configured to engage a mating thread pattern of the drive wheel (e.g., similar to drive wheel 160 depicted in FIGS. 8 and 11). Accordingly, the incremental rotation of the drive wheel 160 (FIG. 8) can be translated into an incremental longitudinal motion for the pushrod 670. Similar to previously described embodiments, when a segment 672 is forwardly advanced through the drive wheel 160, the segment 672 adjusts toward the immediately forward segment 672 so that a leading face 671 of one segment 672 abuts the trailing face 679 of the adjacent segment 672.

Figure 17A:
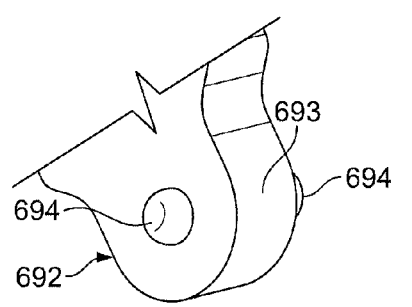
FIGS. 17A-B are perspective views of a portion of the flexible pushrod of FIG. 16.
Figure 17B:
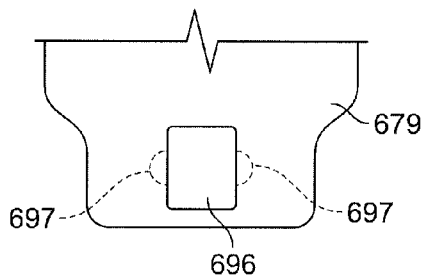

Referring to FIG. 16 and to FIGS. 17A-B, the plurality of segments 672 can be formed from a moldable material, including one or more polymer materials such as Nylon or POM, and then assembled together using the snap hinge assemblies 690. For example, the hinge protrusion 692 of hinge assembly 690 can be inserted into the mating cavity 696 of the adjacent pushrod segment 672 so that the two segments 672 are hingedly engaged with one another. As shown in FIG. 17A, the hinge protrusion 692 may include an extension body 693 that extends from the leading face 671 of the first pushrod segment 672. In this embodiment, locking structures 694 in the form of opposing semi-spherical orbs may extend laterally from extension body 693. As shown in FIG. 17B, the mating cavity 696 extending into the trailing face 679 of the pushrod segment 672 may include sockets 697 therein to receive the locking structures 694 of the hinge protrusion 692. Accordingly, the hinge protrusion 692 (FIG. 17A) can be inserted into the mating cavity 696 (FIG. 17B) so that the locking structures 694 snap into engagement with the sockets 697, thereby providing the hinged coupling between the two segments 672.

Referring again to FIG. 16, the pushrod 670 may be equipped with an anti-torsion mechanism 680 to resist relative twisting motion between adjacent segments 672. Similar to embodiments previously described in connection with FIGS. 13A-B, the anti-torsion mechanism 680 can include an integrally formed protrusion 682 that extends from the leading face 671 of a first segment 672. Also in this embodiment, the anti-torsion mechanism 680 also includes a cavity 683 formed in the trailing face 679 of a second adjacent segment 672. The cavity 683 is configured to mate with the protrusion 682 when this portion of the pushrod 670 is adjusted to a rigid condition in which the leading face 671 of the first segment 672 abuts with the trailing face 679 of the adjacent forward segment 672. As previously described, such an engagement of the components of the anti-torsion mechanism 680 enables the flexible pushrod 670 to hinder the twisting motion of the first segment 672 relative to the adjacent segment 672. Accordingly, the anti-torsion mechanism 680 may oppose torsion of one rod segment 672 relative to its adjacent rod segment 672. By opposing such torsion, the anti-torsion mechanism 680 can resist the torsion stresses that might ordinarily occur across the hinge portion 675.

Optionally, in addition to the anti-torsion mechanism 680, the flexible pushrod 670 can include an anti-rotation mechanism that hinders the pushrod 670 from rotating with drive wheel 160 (FIG. 8). In this embodiment, the anti-rotation mechanism includes two longitudinal channels (only one channel 673 is shown in the view in FIG. 16) that engage respective protrusions on the frame portion 114 (as previously described in connection with FIG. 12). Because the drive wheel 160 can rotate relative to the pushrod 670 (which is substantially prevented from rotating by the anti-rotation mechanism), the rotation of the drive wheel can thereby translate into the longitudinal motion of the pushrod 670.

In some embodiments, the flexible pushrod 670 may include an anti-elongation mechanism that maintains of the pushrod segments 672 in an abutting relationship after that portion of the pushrod 670 has been adjust to the rigid and generally non-curved shape. For example, similar to the embodiments previously described in connection with FIG. 13B, the anti-elongation mechanism may comprise a pressure-sensitive adhesive disposed on the trailing face 679 or leading face 671 of the pushrod segments 672 or may be incorporated into the anti-torsion mechanism 680.

Figure 18:
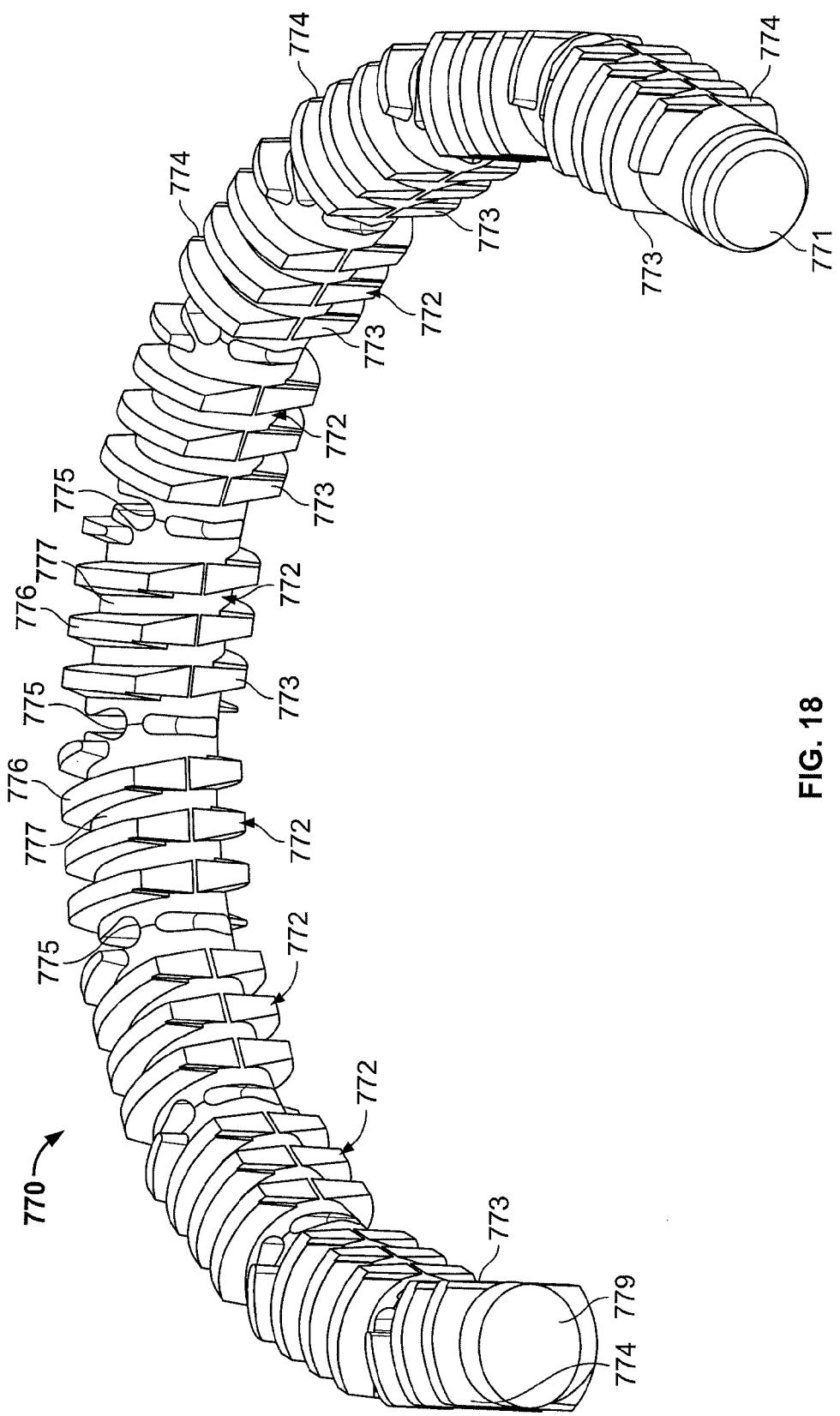
FIG. 18 is a perspective view of a flexible pushrod in accordance with some embodiments.

Referring now to FIG. 18, some embodiments of a flexible pushrod 770 for use in the pump device 100 may include an anti-rotation mechanism other than longitudinal channels. For example, the flexible pushrod 770 may include one or more generally flat lateral faces (e.g., opposing flat faces 773 and 774 are included in this embodiment). In such circumstances, the generally flat lateral faces 773 and 774 can engage complementary flat walls on the frame portion 114 (rather than the protrusions 111a and 111b previously described in connection with FIG. 12).

Similar to previously described embodiments, the flexible pushrod 770 may comprise a plurality of segments 772 serially connected by hinge portions 775 so that the flexible pushrod 770 is adjustable from a curved shape to a noncurved shape. Thus, each segment 772 can pivot toward or away from the adjacent segment 772 so that a portion the flexible pushrod 770 takes on the curved shape or the noncurved shape. The plurality of segments 772 may comprise a thread pattern 776 along at least one cylindrical surface portion 777. Similar to previously described embodiments, the thread pattern 776 may be configured to engage a mating thread pattern of the drive wheel (e.g., similar to drive wheel 160 depicted in FIGS. 8 and 11). Accordingly, the incremental rotation of the drive wheel 160 (FIG. 8) can be translated into an incremental longitudinal motion for the pushrod 770. As previously described, when a segment 772 is forwardly advanced through the drive wheel 160, the segment 772 adjusts toward the immediately forward segment 772 so that a leading face 771 of one segment 772 abuts the trailing face 779 of the adjacent segment 772.

Still referring to FIG. 18, the lateral faces 773 and 774 of the anti-rotation mechanism can be used to hinder the pushrod 770 from rotating with drive wheel 160 (FIGS. 8 and 11). In such circumstances, the drive wheel 160 can rotate about its axis while the anti-rotation mechanism opposes rotation of the pushrod 770 about the longitudinal axis of the pushrod 770. In this embodiment, the lateral faces 773 and 774 comprise generally flat lateral sides formed in the thread pattern 776 of each pushrod segment 772. As such, the thread pattern 776 on each segment 772 may be discontinuous. In this embodiment, the generally flat lateral sides formed in the thread pattern 776 may be formed into a lateral section of the thread pattern 776 that reaches to the depth of the cylindrical surface portion 777. Accordingly, in this embodiment, the lateral faces 773 and 774 do not cut substantially into the cylindrical body of the segment 772, but instead are generally defined along the flat sides of the thread pattern 776. In such circumstances, the generally flat lateral faces 773 and 774 can engage complementary flat walls on the frame portion 114 (rather than the protrusions 111a and 111b previously described in connection with FIG. 12). Because the drive wheel 160 (FIGS. 8 and 11) can rotate relative to the pushrod 770 (which is substantially prevented from rotating by the anti-rotation mechanism), the rotation of the drive wheel 160 can thereby translate into the longitudinal motion of the pushrod 770. It should be understood that, in some embodiments, the lateral faces 773 and 774 may be formed to a depth that cuts into the cylindrical body of the segment 772 and into the thread pattern 776.

Optionally, in addition to the anti-rotation mechanism, the flexible pushrod 770 can include an anti-torsion mechanism to resist such relative twisting motion between adjacent rod segments 772. In such circumstances, the anti-torsion mechanism may include protrusions that engage mating cavities as previously described in connection with FIGS. 13A-B. Thus, the anti-torsion mechanism of the flexible pushrod 770 can resist the torsion stresses that might ordinarily occur across the hinge portion 775.

In some embodiments, the flexible pushrod 770 may include an anti-elongation mechanism that maintains of the pushrod segments 772 in an abutting relationship after that portion of the pushrod 770 has been adjust to the rigid and generally non-curved shape. For example, similar to the embodiments previously described in connection with FIG. 13B, the anti-elongation mechanism may comprise a pressure-sensitive adhesive disposed on the trailing face 779 or leading face 771 of the pushrod segments 772.

Figure 19:
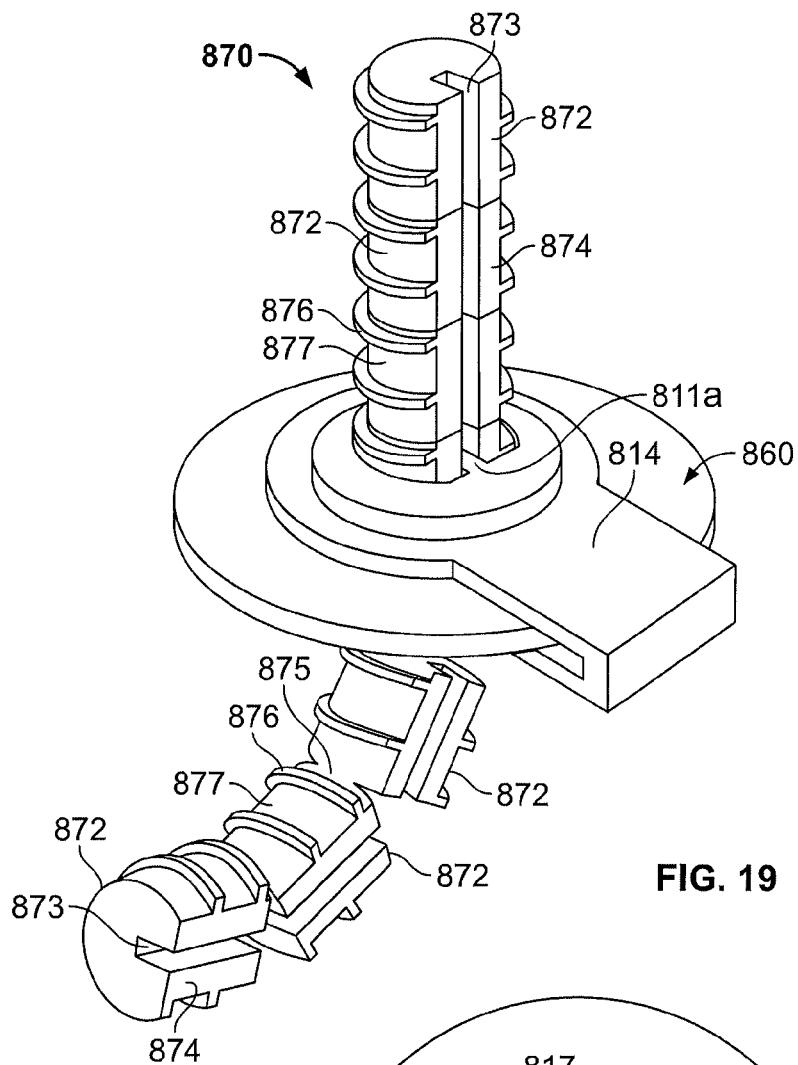
FIGS. 19-20 are perspective views of a flexible pushrod in accordance with some embodiments.
Figure 20:
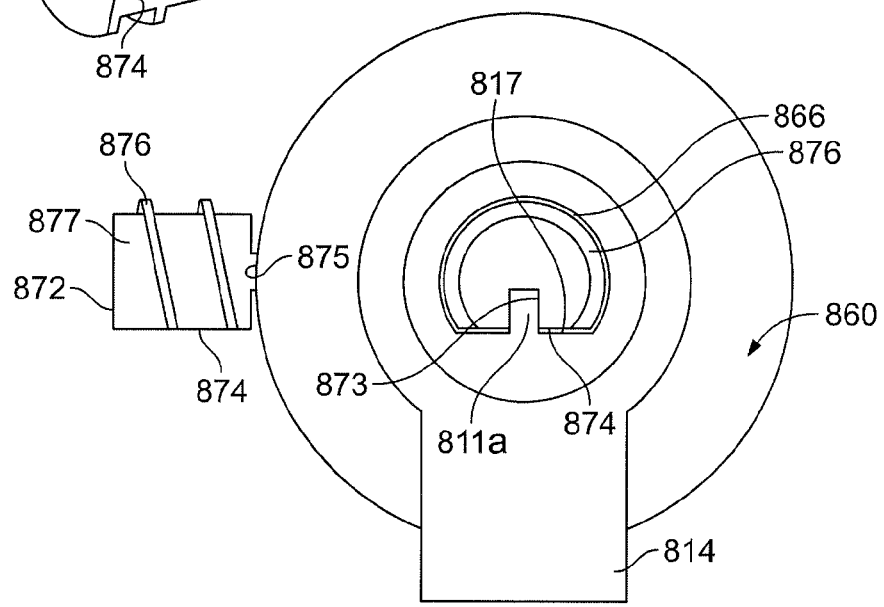

Referring now to FIGS. 19-20, some embodiments of a flexible pushrod 870 for use in the pump device 100 may include an anti-rotation mechanism that includes a combination of one or more longitudinal channels and one or more flat lateral side. In this embodiment, the anti-rotation mechanism of the flexible pushrod 870 includes one longitudinal channel 873 and is formed in one generally flat lateral face 874. In such circumstances, one or both of the longitudinal channel 873 or the generally flat lateral face 874 can engage complementary structure fixed to the frame portion 114.

Similar to previously described embodiments, the flexible pushrod 870 may comprise a plurality of segments 872 serially connected by hinge portions 875 so that the flexible pushrod 870 is adjustable from a curved shape to a noncurved shape. For example, each segment 872 can pivot toward or away from the adjacent segment 872 so that a portion the flexible pushrod 870 takes on the curved shape or the non-curved shape. The plurality of segments 872 may comprise a thread pattern 876 along at least one cylindrical surface portion 877. Similar to previously described embodiments, the thread pattern 876 may be configured to engage a mating thread pattern 866 (FIG. 20) of the drive wheel 860. Accordingly, the incremental rotation of the drive wheel 860 can be translated into an incremental longitudinal motion for the pushrod 870. In this embodiment, the drive wheel 860 may include a fixed portion 814 that can be mounted to the frame portion 114 of the pump device 100. Similar to previously described embodiments, when a segment 872 is forwardly advanced through the drive wheel 860, the segment 872 adjusts toward the immediately forward segment 872 so that a leading face 871 of one segment 872 abuts the trailing face 879 of the adjacent segment 872.

Still referring to FIGS. 19-20, one or both of the longitudinal channel 873 or the lateral side 874 can be used to hinder the pushrod 870 from rotating with drive wheel 860. In this embodiment, the lateral face 874 of the anti-rotation mechanism is formed to a depth that cuts into both the thread pattern 876 and the cylindrical body of each rod segment 872. As such, the thread pattern 876 on each segment 872 may be discontinuous. In such circumstances, the generally flat lateral face 874 can engage a complementary flat wall 817 on the fixed portion 814 that is mounted to the frame of the pump device 100. In addition, the longitudinal channel 873 of the anti-rotation mechanism can engage protrusion 811a on the fixed portion 814 (mounted to the frame of the pump device 100). Because the drive wheel 860 can rotate relative to the pushrod 870 (which is substantially prevented from rotating by the anti-rotation mechanism), the rotation of the drive wheel 860 can thereby translate into the longitudinal motion of the pushrod 870. It should be understood that, in some embodiments, the flexible pushrod 870 may include two opposing longitudinal channels 873 that are formed respectively in two opposing lateral faces 874.

Optionally, in addition to the anti-rotation mechanism, the flexible pushrod 870 can include an anti-torsion mechanism to resist such relative twisting motion between adjacent rod segments 872. In such circumstances, the anti-torsion mechanism may include protrusions that engage mating cavities as previously described in connection with FIGS. 13A-B. Thus, the anti-torsion mechanism of the flexible pushrod 870 can resist the torsion stresses that might ordinarily occur across the hinge portion 875.

In some embodiments, the flexible pushrod 870 may include an anti-elongation mechanism that maintains of the pushrod segments 872 in an abutting relationship after that portion of the pushrod 870 has been adjust to the rigid and generally non-curved shape. For example, similar to the embodiments previously described in connection with FIG. 13B, the anti-elongation mechanism may comprise a pressure-sensitive adhesive disposed on the trailing face 879 or leading face 871 of the pushrod segments 872.

A number of embodiments of the invention have been described. Nevertheless, it will be understood that various modifications may be made without departing from the spirit and scope of the invention. Accordingly, other embodiments are within the scope of the following claims.

What is claimed is:

1. An infusion pump system for the delivery of medication, comprising:
 a pump housing defining a space to receive a medicine for dispensation; and
 a drive system to dispense medicine when the medicine is received by the pump housing, the drive system including a pushrod that is movable to apply a dispensing force to dispense medicine,
 the pushrod including rod segments that are hingedly engaged to one another such that at least a portion of the pushrod is adjustable from a curved shape to a generally noncurved shape,
 the pushrod including an anti-elongation mechanism disposed on at least a plurality of the pushrod segments to maintain the leading face of one pushrod segment in abutting relationship with a trailing face of an adjacent pushrod segment when a portion of the pushrod is adjusted to the generally noncurved shape.

2. The system of claim 1, wherein the anti-elongation mechanism comprises a pressure sensitive adhesive disposed on the pushrod segments.

3. The system of claim 2, wherein the pressure sensitive adhesive is disposed on at least one of the leading face of the one pushrod segment and the trailing face of the adjacent pushrod segment.

4. The system of claim 3, wherein the pressure sensitive adhesive affixes the leading face of the one pushrod segment to the trailing face of the adjacent pushrod segment when the leading face abuts with the trailing face.

5. The system of claim 1, wherein pushrod further comprises an anti-torsion mechanism that opposes torsion of the one pushrod segment relative to another pushrod segment.

6. The system of claim 5, wherein the anti-torsion mechanism comprises an extended member protruding from the one rod segment that is engageable with a cavity disposed in the adjacent rod segment, the extended member being received into the cavity when at least a portion of the pushrod is adjusted to the generally noncurved shape.

7. The system of claim 1, wherein the pushrod further comprises an anti-rotation mechanism to oppose rotation of the pushrod about a longitudinal axis of the pushrod.

8. The system of claim 7, wherein the anti-rotation mechanism comprises one or more longitudinal channels extending through at least a plurality of the rod segments.

9. The system of claim 7, wherein the anti-rotation mechanism comprises at least one flat surface along the lateral side of at least a plurality of the rod segments.

10. The system of claim 1, wherein the space defined by the pump housing is operable to receive a medicine container that contains medicine.

11. The system of claim 10, wherein the medicine container is a carpule that is preloaded with insulin, the carpule including a penetratable septum at an output end.

12. A method delivering of medication from an infusion pump system, comprising:
receiving a supply of medicine in an interior space of a pump housing; and
activating a drive system to dispense at least a portion of the medicine through a tubular member away from the pump housing, the drive system including a pushrod that is urged toward the supply of the medicine to apply a dispensing force to dispense the medicine, wherein the pushrod includes rod segments that are hingedly engaged to one another such that at least a portion of the pushrod is adjustable from a curved shape to a generally noncurved shape, the pushrod further including an anti-elongation mechanism disposed on at least a plurality of the pushrod segments to maintain the leading face of one pushrod segment in abutting relationship with a trailing face of an adjacent pushrod segment when a portion of the pushrod is adjusted to the generally noncurved shape.

13. The method of claim 12, wherein the step of activating the drive system causes at least a portion of the pushrod to forwardly advance toward the generally noncurved shape, and wherein the anti-elongation mechanism comprises a pressure sensitive adhesive disposed on the pushrod segments.

14. The method of claim 13, wherein the pressure sensitive adhesive is disposed on at least one of the leading face of the one pushrod segment and the trailing face of the adjacent pushrod segment.

15. The method of claim 14, wherein the pressure sensitive adhesive affixes the leading face of the one pushrod segment to the trailing face of the adjacent pushrod segment when the leading face abuts with the trailing face.

16. The method of claim 12, wherein the step of activating the drive system causes a rotatable element to rotate relative to a longitudinal axis of the pushrod, and wherein pushrod further comprises an anti-torsion mechanism that opposes torsion of the one pushrod segment relative to another pushrod segment.

17. The method of claim 16, wherein the anti-torsion mechanism comprises an extended member protruding from the one rod segment that is engageable with a cavity disposed in the adjacent rod segment, the extended member being received into the cavity when at least a portion of the pushrod is adjusted to the generally noncurved shape.

18. The method of claim 12, wherein the step of activating the drive system causes a rotatable element to rotate relative to a longitudinal axis of the pushrod, and wherein the pushrod further comprises an anti-rotation mechanism to oppose rotation of the pushrod about a longitudinal axis of the pushrod.

19. The method of claim 18, wherein the anti-rotation mechanism comprises one or more longitudinal channels extending through at least a plurality of the rod segments.

20. The method of claim 18, wherein the anti-rotation mechanism comprises at least one flat surface along the lateral side of at least a plurality of the rod segments.

* * * * *